US012637665B2

(12) United States Patent
Coronel et al.

(10) Patent No.: US 12,637,665 B2
(45) Date of Patent: May 26, 2026

(54) METHOD FOR THE PRODUCTION OF AAV

(71) Applicant: Cevec Pharmaceuticals GmbH,
Cologne (DE)

(72) Inventors: Juliana Coronel, Cologne (DE); Silke Wissing, Marburg (DE)

(73) Assignee: Cevec Pharmaceuticals GmbH,
Cologne (DE)

( * ) Notice: Subject to any disclaimer, the term of this patent is extended or adjusted under 35 U.S.C. 154(b) by 664 days.

(21) Appl. No.: 18/005,027

(22) PCT Filed: Nov. 23, 2021

(86) PCT No.: PCT/EP2021/082615
§ 371 (c)(1),
(2) Date: Jan. 10, 2023

(87) PCT Pub. No.: WO2022/112218
PCT Pub. Date: Jun. 2, 2022

(65) Prior Publication Data
US 2024/0263148 A1     Aug. 8, 2024

(30) Foreign Application Priority Data

Nov. 25, 2020     (EP) ..................................... 20209811

(51) Int. Cl.
| *C12N 7/00* | (2006.01) |
| *C12M 1/00* | (2006.01) |
| *C12N 15/86* | (2006.01) |

(52) U.S. Cl.
CPC .............. *C12N 7/00* (2013.01); *C12M 29/10* (2013.01); *C12N 15/86* (2013.01);
(Continued)

(58) Field of Classification Search
None
See application file for complete search history.

(56) References Cited

U.S. PATENT DOCUMENTS

| 6,844,192 B2 | 1/2005 | Orlando et al. |
| 6,989,264 B2 | 1/2006 | Atkinson et al. |
| | (Continued) | |

FOREIGN PATENT DOCUMENTS

| RU | 2772989 C2 | 5/2022 | |
| WO | WO-0024916 A1 * | 5/2000 | ............. C12N 15/86 |
| | (Continued) | | |

OTHER PUBLICATIONS

Merten et al., "AAV vector production: state of the art developments and remaining challenges," Cell Gene Therapy Insights, 2(5): 521-551 (Year: 2016).*
(Continued)

*Primary Examiner* — M Franco G Salvoza
(74) *Attorney, Agent, or Firm* — Eversheds-Sutherland (US) LLP

(57) ABSTRACT

The present invention relates to methods for the production of Adeno-associated virus (AAV), comprising steps of providing a stable AAV producer cell line in which at least some or all genes encoding the components necessary for the production of AAV are stably integrated into the cell genome, and culturing said cells in perfusion culture during the AAV production step (i.e., during the N step), wherein said perfusion culture encompasses continuous replacement of spent media with fresh media, and wherein said continuous replacement of spent media with fresh media continues after the induction of AAV production.

15 Claims, 17 Drawing Sheets

Figure 1:
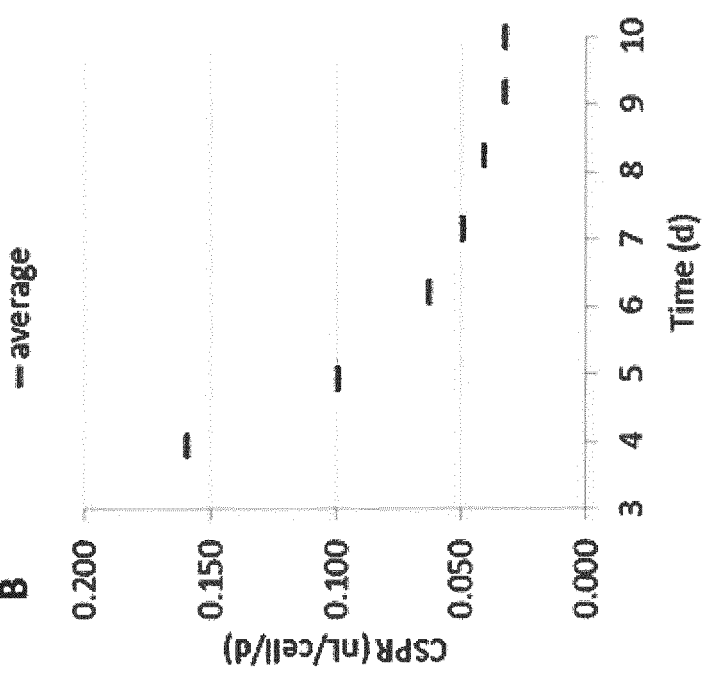
Figure 1:
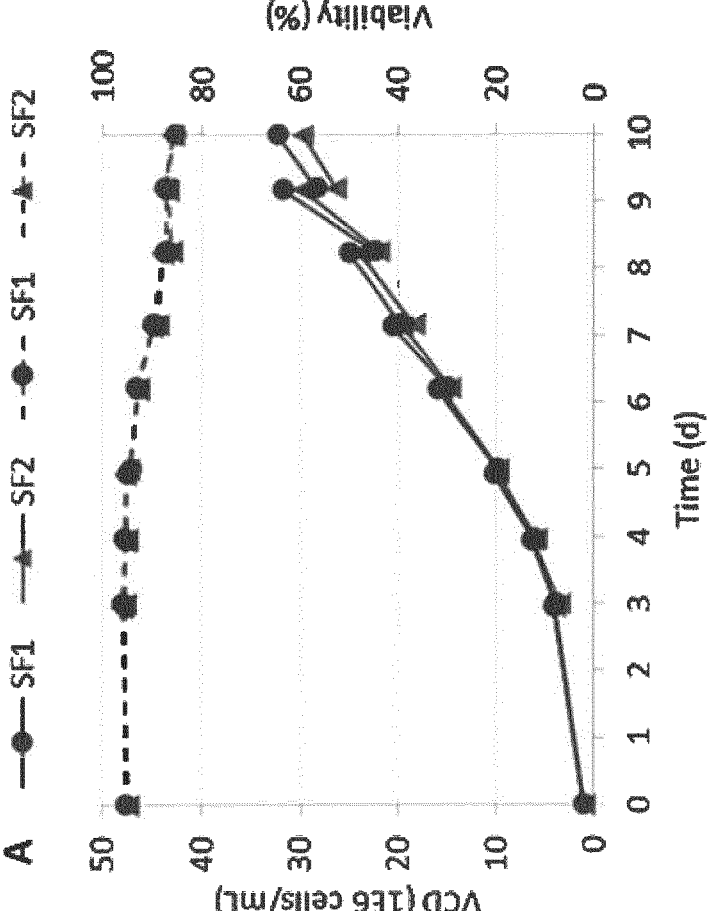
Figure 2:
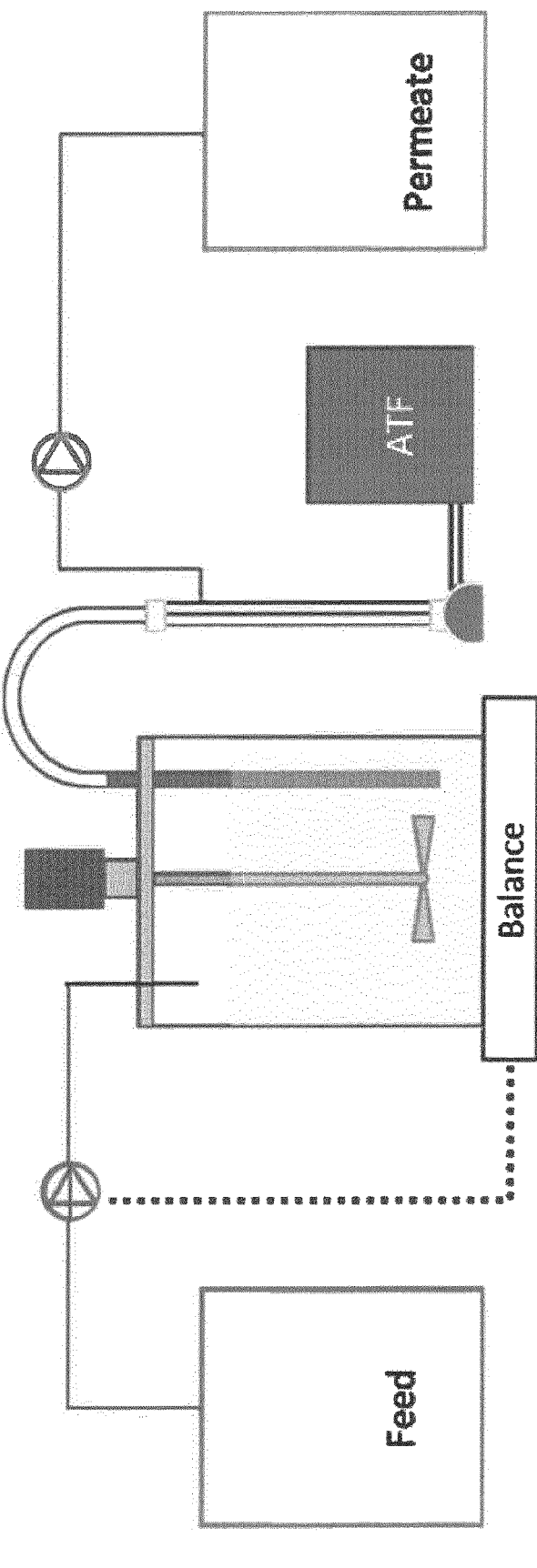

Specification includes a Sequence Listing.

(52) U.S. Cl.
    CPC .............. *C12N 2750/14122* (2013.01); *C12N 2750/14143* (2013.01); *C12N 2750/14152* (2013.01)

(56) References Cited

U.S. PATENT DOCUMENTS

| | | | |
|---|---|---|---|
| 2002/0127582 A1 | 9/2002 | Atkinson et al. | |
| 2002/0168342 A1* | 11/2002 | Wang ................... | C07K 14/005 |
| | | | 435/456 |
| 2014/0242671 A1 | 8/2014 | Grieger | |
| 2017/0292103 A1* | 10/2017 | Cattaneo ............... | C12M 29/16 |
| 2020/0277628 A1 | 9/2020 | Hein et al. | |

FOREIGN PATENT DOCUMENTS

| | | |
|---|---|---|
| WO | WO 03/104392 | 12/2003 |
| WO | WO 2020/154607 | 7/2020 |
| WO | WO 2020/223274 | 11/2020 |

OTHER PUBLICATIONS

Merten, "AAV vector production: state of the art developments and remaining challenges," Cell Gene Therapy Insights, 2(5): 521-551 (Year: 2016).*

Search Report issued in corresponding Israel application No. 296770, mailed Jun. 18, 2023 (10 pages).

Cell & Gene Therapy Insights: Stable AAV producer cell lines, evaluating vector manufacturing, 2020, https://vimeo.com/417208805.

Cehajic-Kapetanovic et al., Gene therapy for the special senses 1. Retinal gene therapy in X-linked retinitis pigmentosa cause by . . . , 2020, ASGCT 23rd Ann Mtg Abst 454.

Office Action issued in corresponding Canadian application No. 3174017, mailed Aug. 25, 2023 (12 pages).

Goncalves, I. et al., "Development of a Stable Helper Virus Free Producer Cell Line for Scalable Adeno-Associated Virus Vectors Production Based on Human Suspension Cells", American Society of Gene & Cell Therapy 23rd Annual Meeting, Abstract 454, Apr. 28, 2020 (Apr. 28, 2020), https://annualmeeting.asgct.org/am20/abstracts, [Retrieved from the internet on Aug. 22, 2023 (Aug. 22, 2023)].

Hein, K. et al., "Establishment of a Scalable Production Process Using Stable HelperVirus Free AAV Producer Cell Lines Based on Human Suspension Cells", American Society of Gene & Cell Therapy 23rd Annual Meeting, Abstract 464, Apr. 28, 2020 (Apr. 28, 2020), https://annualmeeting.asgct.org/am20/abstracts, [Retrieved from the internet on Aug. 22, 2023 (Aug. 22, 2023)].

Lackner et al., Studies of the mechanism of transactivation of the adeno-associated virus p19 promoter by the Rep protein, 2002, J. Virol. vol. 76, pp. 8225-8235.

RU Office Action and Search Report for corresponding RU Application No. 2022126842, dated Apr. 17, 2025, 15 pages.

First Japanese Office Action for JP Application No. 2024-111946, dated Nov. 4, 2025 (8 pages, English translation).

Grieger, J.C. et al. "Production of Recombinant Adeno-associated Virus Vectors Using Suspension HEK293 Cells and Continuous Harvest of Vector From the Culture Media for GMP FIX and FLT1 Clinical Vector", Molecular Therapy, 2016, 24(2): pp. 287-297.

Ozawa, K. "Gene therapy using AAV", Jichi Medical University, 2007, 57(1): pp. 47-56.

* cited by examiner

Perfusion
AEX run 2

Perfusion
AEX run 1

METHOD FOR THE PRODUCTION OF AAV

This application is a is a 371 of PCT/EP2018/075158, having an international filing date of Sep. 18, 2018, which claims the benefit of European Patent Application Serial No. 17001562.2, filed Sep. 19, 2017, the content of which is incorporated by reference in its entirety.

The official copy of the Sequence Listing is submitted concurrently with the specification as an xml file, made with WIPO Sequence Version 2.1.0, via EFS-Web, with a file name of "CVC009.xml", a creation date of Dec. 5, 2022, and a size of 8 kilobytes. The Sequence Listing filed via EFS-Web is part of the specification and is incorporated in its entirety by reference herein.

The present invention relates to methods for the production of Adeno-associated virus (AAV), comprising steps of providing a stable AAV producer cell line in which at least some or all genes encoding the components necessary for the production of AAV are stably integrated into the cell genome, and culturing said cells in perfusion culture during the AAV production step (i.e., during the N step), wherein said perfusion culture encompasses continuous replacement of spent media with fresh media, and wherein said continuous replacement of spent media with fresh media continues after the induction of AAV production.

Recently there has been a rapid increase in the number of gene therapy trials and products based on AAV-derived vectors. Advantages of AAV vectors in gene therapy are a good safety profile, the fact that such vectors are not pathogenic, i.e., are not associated with any disease, the long-term expression of transgenes, and the possibility of transducing dividing as well as non-dividing cells. However, a major challenge for translation of this promising research to clinical development is the challenge to deliver substantial amounts of AAV viral vectors in high quality.

The production of recombinant AAV inter alia requires the expression of AAV Rep and Cap proteins, usually encoded by the AAV genome, for production of recombinant virus supplied in trans. Further, helper genes are used which can be derived from different helper viruses, the most common being helper virus genes taken from Adenovirus (AV), such as E1A, E1B, E2A, E4orf6, or VA RNA. Furthermore, a transfer vector containing the gene of interest (GOI) flanked by AAV inverted terminal repeat sequences (ITRs) is needed.

Current production systems for AAV rely mostly on the following techniques which, however, have several drawbacks.

The most common system for the production of recombinant AAV relies on the introduction of all genes necessary for AAV production into the production cells by transient transfection. Transient transfection usually requires a two- or three-plasmid system: transfer vector containing gene of interest; pHelper with adenoviral helper functions; and pAAV-Rep2CapX (CapX=capsid function of different AAV serotypes) supplying the capsid and replicase functions. However, this approach has several drawbacks. In particular, due to the transient transfection step, this method entails high costs of plasmid DNA and lacks sufficient scalability, robustness, and reproducibility.

In addition, the transient transfection step impedes certain process optimization steps to increase product titer or product quality which are common in the production of other recombinant biologicals, like extensive media and feed optimization, and variation of process parameters like pH, temperature, or cell density during production. In particular the latter one is a promising approach to increase the overall product titer. A higher cell density in general leads to an increased titer, as long as cell specific productivity is not decreased ("cell-density effect"). In particular while using transient transfection, the cell specific productivity can decrease while increasing cell density. This is also described in particular for the production of viral vectors.

Production of AAV results, independently of the particular production process, always in a mixture of full AAV particles, that means with the packaged gene of interest (GOI) flanked by AAV ITRs and empty particles without the packaged GOI. AAV titers achieved by transient transfection of mammalian suspension cells, such as e.g. HEK293 cells, are in the range of $1 \times 10^{13}$ to $1 \times 10^{15}$ vg/L (viral genomes per L) depending on the process. By transient transfection the proportion of full particles was reported with a maximum of ~30% full particles, but is normally in the range of 10-18%. This implies that 82-90% are undesirable empty particles. Empty particles are therapeutically inactive and can increase immune responses in the patients. Therefore, in the purification process post-production, these empty particles have to be removed as efficiently as possible. This can be achieved either via centrifugation, a process which is effective but not scalable, or by chromatography methods. The latter can be utilized also for large scale production but the fold enrichment of full particle is normally only in the range of ≈3- to 6-fold. Therefore, e.g. the enrichment of a sample with around 10% full particles results in a final proportion of only ≈30 to 60% full particles.

So-called producer cell lines with an already stably integrated gene of interest are mostly based on HEK or Hela cells. However, they need additional infection with helper virus, e.g. adenovirus. This addition of helper virus during AAV production requires first production of the corresponding helper virus, then extensive purification of the produced AAV vector in order to remove the helper virus from the final product and costly proof of absence of helper viruses. The same applies for Herpes simplex virus (HSV)-based system. The Baculovirus-based system additionally lacks sufficient scalability and robustness, and adds the risk of contaminations by insect host cell protein and immunogenic insect cell specific glycosylation structures.

Therefore, current AAV production systems are limited not only with respect to scalability, robustness, reproducibility, ease of use and cost efficiency but also in respect to product quality.

Accordingly, the technical problem underlying the present invention is the provision of a scalable system for the stable production of AAV vectors that does not require transient transfection or helper viruses, allowing for the robust, industrial and scalable production of AAV gene therapy vectors, as well as extensive upstream process development optimization, in particular with the aim to increase product titer and/or cell specific yield, and even more importantly product quality, in particular in terms of the proportion of full particles.

The solution to the above technical problem is achieved by the embodiments characterized in the claims.

In particular, in a first aspect, the present invention relates to a method for the production of Adeno-associated virus (AAV), comprising the steps of:

(a) providing a stable AAV producer host cell line in which at least some or all genes encoding the components necessary for the production of AAV are stably integrated into the host cell genome;

(b) culturing said cells in perfusion culture during the AAV production step (i.e., during the N step), wherein said perfusion culture encompasses continuous replacement of spent media with fresh media, and wherein said continuous replacement of spent media with fresh media continues after the induction of AAV production.

AAV in the present invention is not limited to particular AAV serotypes. Thus, AAV can be selected from the group consisting of AAV serotype 1 (AAV1), AAV2, AAV3, AAV4, AAV5, AAV6, AAV7, AAV8, AAV9, AAV10, AAV11, AAVDJ, AAVDJ8, AAVrh10, hybrids of two or more different of said serotypes, and said serotypes having mutations that alter the tropism of the AAV serotype. Preferably, AAV is selected from the group consisting of AAV2, AAV5, AAV6, AAV8, and AAV9, wherein AAV8 is particularly preferred.

According to the present invention, at least some or all genes encoding the components necessary for the production of AAV are stably integrated into the host cell genome. Preferably, at least 2, at least 3, at least 4, at least 5, at least 6, or all of said genes are stably integrated into the host cell genome. More preferably, all of said genes are stably integrated into the host cell genome.

In this context, according to the present invention, the genes encoding the components necessary for the production of AAV are selected from the group consisting of genes encoding the AAV Cap proteins VP1, VP2, and VP3; genes encoding the AAV Rep proteins Rep78, Rep68, Rep52, and Rep40; genes encoding the adenoviral helper functions E4orf6, E2A and VA-RNA; genes encoding the Ad5 helper genes E1A and E1B; and the gene of interest (GOI) flanked by AAV ITRs. Preferably, the genes encoding the components necessary for the production of AAV include the genes encoding the AAV Cap proteins VP1, VP2, and VP3; a gene encoding the AAV Rep protein Rep78 or Rep68, a gene encoding the AAV Rep protein Rep52 or Rep40; a gene encoding the adenoviral helper function E4orf6, and the gene of interest (GOI) flanked by AAV ITRs. In specific embodiments, the genes encoding the components necessary for the production of AAV additionally include at least 1, at least 2, at least 3, at least 4, at least 5, or all of the genes encoding the AAV Rep protein Rep78, Rep68, Rep52 and Rep40; and the genes encoding the adenoviral helper functions E2A and VA-RNA; and the genes encoding the Ad5 helper genes E1A and E1B.

Thus, in specific embodiments, in the stable AAV producer host cell line provided in step (a) of the methods of the present invention, the following genes are stably integrated into the host cell genome:
  a gene encoding the AAV Rep protein Rep78 or Rep68,
  a gene encoding the AAV Rep protein Rep52 or Rep40; and
  the genes encoding the adenoviral helper functions E4orf6 and E2A.

In other specific embodiments, in the stable AAV producer host cell line provided in step (a) of the methods of the present invention, the following genes are stably integrated into the host cell genome:
  the genes encoding the AAV Cap proteins VP1, VP2, and VP3;
  a gene encoding the AAV Rep protein Rep78 or Rep68,
  a gene encoding the AAV Rep protein Rep52 or Rep40;
  the genes encoding the adenoviral helper functions E4orf6 and E2A, and
  the gene of interest (GOI) flanked by AAV ITRs.

In yet further specific embodiments, in the stable AAV producer host cell line provided in step (a) of the methods of the present invention, the following genes are stably integrated into the host cell genome:

the genes encoding the AAV Cap proteins VP1, VP2, and VP3;
  a gene or genes encoding either one or both of the AAV Rep proteins Rep78 or Rep68,
  a gene or genes encoding either one or both of the AAV Rep proteins Rep52 or Rep40;
  the gene of interest (GOI) flanked by AAV ITRs; and
  optionally, a gene or genes encoding either one, either two, either three, or all of the adenoviral helper functions E1A, E1B, E4orf6 and E2A.

In related specific embodiments, in the stable AAV producer host cell line provided in step (a) of the methods of the present invention, the following genes are stably integrated into the host cell genome:
  (i) the genes encoding the AAV Cap proteins VP1, VP2, and VP3; a gene encoding the AAV Rep protein Rep78 or Rep68, a gene encoding the AAV Rep protein Rep52 or Rep40; and the gene of interest (GOI) flanked by AAV ITRs; or
  (ii) the genes encoding the AAV Cap proteins VP1, VP2, and VP3; a gene encoding the AAV Rep protein Rep78 or Rep68, a gene encoding the AAV Rep protein Rep52 or Rep40; a gene encoding the adenoviral helper function E4orf6, and the gene of interest (GOI) flanked by AAV ITRs; or
  (iii) the genes encoding the AAV Cap proteins VP1, VP2, and VP3; a gene encoding the AAV Rep protein Rep78 or Rep68, a gene encoding the AAV Rep protein Rep52 or Rep40; genes encoding the adenoviral helper functions E4orf6 and E2A, and the gene of interest (GOI) flanked by AAV ITRs; or
  (iv) the genes encoding the AAV Cap proteins VP1, VP2, and VP3; a gene encoding the AAV Rep protein Rep78 or Rep68, a gene encoding the AAV Rep protein Rep52 or Rep40; genes encoding the adenoviral helper functions E1A, E1B, E4orf6 and E2A, and the gene of interest (GOI) flanked by AAV ITRs; or
  (v) the genes encoding the AAV Cap proteins VP1, VP2, and VP3; the genes encoding the AAV Rep proteins Rep78, Rep68, Rep52 and Rep40; the genes encoding the adenoviral helper functions E4orf6 and E2A; and the gene of interest (GOI) flanked by AAV ITRs; or
  (vi) the genes encoding the AAV Cap proteins VP1, VP2, and VP3; the genes encoding the AAV Rep proteins Rep78, Rep68, Rep52 and Rep40; the genes encoding the adenoviral helper functions E1A, E1B, E4orf6 and E2A; and the gene of interest (GOI) flanked by AAV ITRs.

In one specific embodiment, the method for the production of AAV according to the present invention comprises the steps of:
  (a) providing a stable AAV producer host cell line in which at least some or all genes encoding the components necessary for the production of AAV are stably integrated into the host cell genome;
  (b) culturing said cells in perfusion culture during the AAV production step (i.e., during the N step), wherein said perfusion culture encompasses continuous replacement of spent media with fresh media, and wherein said continuous replacement of spent media with fresh media continues after the induction of AAV production,
wherein at least the following genes are stably integrated into the host cell genome: the genes encoding the AAV Cap proteins VP1, VP2, and VP3;
  a gene encoding the AAV Rep protein Rep78 or Rep68,
  a gene encoding the AAV Rep protein Rep52 or Rep40;

the genes encoding the adenoviral helper functions E4orf6
and E2A, and
the gene of interest (GOI) flanked by AAV ITRs.

In this specific embodiment, the following additional
genes can be stably integrated into the host cell genome:
the genes encoding both of the AAV Rep proteins Rep78
and Rep68,
the genes encoding both of the AAV Rep proteins Rep52
and Rep40; and
a gene or genes encoding either one or both of the
adenoviral helper functions E1A, E1B.

GOIs to be used in the context of the present invention are
not particularly limited and include any genes the transfer of
which into the recipient of the AAV vector is of interest, e.g.
for treatment of eye diseases, blindness diseases, muscular
diseases, Duchenne muscular dystrophy, GM2 gangliosido-
sis and spinocerebellar ataxia type, ALS, Huntington dis-
ease, X-linked severe combined immunodeficiency
(X-SCID), adenosine deaminase deficiency (ADA-SCID),
central nervous system diseases, Parkinson's disease,
Alzheimer disease, liver diseases, liver enzyme ornithine
transcarbamylase (OTC) deficiency, Leber's congenital
amaurosis, hemophilia, $\beta$-thalassemia, cancer diseases, head
and neck cancer, metastatic melanoma, heart diseases, lung
diseases, or cystic fibrosis, Wiskott-Aldrich syndrome
(WAS), metachromatic leukodystrophy (MLD), and severe
lipoprotein lipase deficiency disorder (LPLD) infection dis-
eases, severe combined immunodeficiency syndrome, HIV
infection, rare diseases including Niemann Pick Disease
Type C and ornithine transcarbamylase (OTC) deficiency.

The stable AAV producer host cell line used in the present
invention can be derived from any suitable cell line known
in the art. However, in preferred embodiments, said cell line
is derived from a cell line, or is a cell line, selected from the
group consisting of CAP cells, AGE1.hn, HEK293, PER.C6,
NSO1, COS-7, BHK, CHO, CV1, VERO, HeLa, MDCK,
BRL3A, W138, and HepG2 cells, wherein CAP cells and
HEK293 cells are particularly preferred. In a specific
embodiment, the above cell line is derived from CAP cells
or is a CAP cell line. In another specific embodiment, the
above cell line is derived from HEK293 cells or is a
HEK293 cell line. In this context, the term "the stable AAV
producer host cell line is derived from a cell line X"
indicates that said stable AAV producer host cell line is
generated by stably integrating the respective genes indi-
cated above into cells of cell line X. Thus, the above term
expressly encompasses the stable AAV producer host cell
line being a cell line X, as indicated above. In this context,
the term "the stable AAV producer host cell line is derived
from a cell line X" can be read as "the stable AAV producer
host cell line is based on a cell line X", and the respective
terms can be used interchangeably herein.

The scale of AAV production according to the present
invention can vary from small volumes in the milliliter range
over mid-range volumes up-to large scale volumes with e.g.
2,000 L or 25,000 L volume per production run.

Perfusion culture in step (b) of the methods of the present
invention can be performed in any suitable culture vessel or
system known in the art. Different types of bioreactor which
can be used in this respect include stirred-tank bioreactors
(STR), orbitally shaken bioreactors (OSB), rocking bed
bioreactors (e.g. WAVE, Rocking Motion), air-lift bioreactors, or tubular bioreactors. For any of these bioreactor
types, glass, stainless steel or single-use bioreactor vessels
can be used. Also, valid multi-parallel bioreactors, including
high throughput bioreactors coupled to perfusion devices,
can be used. Perfusion bioreactors designed for adherent
cells can also be used, e.g. hollow-fiber bioreactors (HFBR),
fixed-bed bioreactors (e.g. packed-bed bioreactors), and
fluidized bed bioreactors.

Operational modes for perfusion culture include but are
not particularly limited to standard perfusion (continuous),
concentrated perfusion (continuous), hybrid perfusion/fed-
batch, perfusion with volume expansion, and two-stage
continuous processes, as known in the art. Perfusion devices
include hollow-fiber filters operated under strategies such as
TFF (tangential flow filtration) and ATF (alternating tangen-
tial flow), floating membranes, spin-filters and rotating
cylindrical filters (aka vortex-flow filters or external spin-
filters) and rotating disc filters (aka controlled-shear filters),
wherein ATF perfusion culture is particularly preferred.
Other types of filtration devices such as hollow-fiber based
or tubular membrane modules operating with peristaltic
pumps, diaphragm pumps or centrifugal pumps based on
magnetic levitation (e.g. Levitronix) can also be used. Yet
further perfusion devices include gravitational settlers (la-
mella settlers, compact cell settlers), acoustic settlers (aka
acoustic filter), centrifuges, and hydrocyclones, as known in
the art.

According to the present invention, perfusion culture
encompasses continuous replacement of spent media with
fresh media (i.e., continuous medium exchange), wherein
said continuous replacement of spent media with fresh
media continues after the induction of AAV production. In
preferred embodiments, said continuous replacement of
spent media with fresh media continues for at least 24 hours
after induction, at least 48 hours after induction, at least 72
hours after induction, and/or until the harvest of AAV. As
known in the art, the terms "continuous replacement of spent
media with fresh media" or "continuous medium exchange"
do not necessarily require non-stop replacement of spent
media with fresh media (i.e., non-stop medium exchange),
but also allows for pausing said replacement for intervals
several times a day, as known in the art. By way of example,
possible pauses of replacement or medium exchange are
pauses for e.g. up to 1 hour or up to 2 hours, 1, 2, 3, 4, 5 or
6 times a day, or pauses for e.g. up to 6 hours or up to 12
hours, once or twice a day.

In preferred embodiments, the cell specific perfusion rate
(CSPR) during perfusion culture is about 0.01 to about 0.20
nL/cell/day. Further, the perfusion rate is preferably about 1
to about 20 vvd (volume of fresh medium/working volume
of reactor/day).

According to the present invention, the methods can be
initiated with a cell density at seeding at lower viable cell
densities (VCD) in the range of about $0.1 \times 10^6$ to about
$2.0 \times 10^6$ cells/mL, or at higher VCD in the range of about
$2.0 \times 10^6$ to about $20 \times 10^6$ cells/mL. In preferred embodi-
ments, the cell density at the seeding of the perfusion culture
is about $0.5 \times 10^6$ to about $5 \times 10^6$ cells/mL.

Further, the cell density at the timepoint of induction of
AAV production can be at lower VCD in the range of about
$1.0 \times 10^6$ to about $10 \times 10^6$ cells/mL, at high VCD in the range of about $10\times10^6$ to about $100\times10^6$ cells/mL, or at very high VCD in the range of about $100\times10^6$ to about $200\times10^6$ cells/mL. In preferred embodiments, the cell density at the timepoint of the induction of AAV production is about $20\times10^6$ cells/mL or higher.

In specific embodiments, the methods of the present invention can comprise a step of harvesting AAV from the perfusion culture retentate.

In the methods of the present invention, the process time from post-seeding until the induction of AAV production can be in the range of 0 to 21 days. Further, the process time post-induction can be in the range of 2 to 10 days post-induction.

In order to achieve maximum AAV titer, process parameters such as seeding cell density, temperature, stirring speed, pH, DO (dissolved oxygen), osmolarity, and/or bioreactor working volume can be changed during the production process, as known in the art. In addition, in order to avoid deprivation of certain amino acids, saccharides, organic acids, cofactors, vitamins, minerals, and/or other elements, supplementation of the cell culture with the lacking components can be part of the production process, as known in the art.

In a second aspect, the present invention relates to an Adeno-associated virus (AAV), obtainable by the method according to the present invention as defined above.

As used herein, the term "comprising"/"comprises" expressly includes the terms "consisting essentially of"/ "consists essentially of" and "consisting of"/"consists of", i.e., all of said terms are interchangeable with each other.

The term "about" as used herein is a modified of the specified value of ±10%, preferably ±7%, ±5%, ±4%, ±3%, ±2%, ±1%, or ±0.5%. By way of example, the term "about 10" as used herein can refer to a range of 9 to 11.

In the present invention, fully stable AAV producer cell lines represent an effective method for the large-scale manufacturing of AAV vectors. These fully stable AAV producer cells consist of cells with a stable integration of e.g. the capsid genes (VP1, VP2, VP3), regulatory genes (Rep78, Rep68, Rep52, Rep40), adenoviral helper functions (E1A, E1B, E4orf6, E2A and VA-RNA) and the ITR-flanked transgene (gene of interest; GOI). In this system, the expression of the four rep proteins and the helper functions E2A and E4orf6 are under the control of an inducible system. By addition of the inducer, the aforementioned proteins are expressed, and recombinant AAV (rAAV) vectors are produced.

This stable system harbors several advantages, as no transient transfection step or helper infection step is necessary. Therefore, costs of good are reduced due to the omitted plasmid costs or additional cost for the production of helper virus. The system is scalable, highly reproducible with only minor or none batch to batch variations.

Most importantly, the stable AAV production cell line used in the present invention, with no need for transient transfection or virus infection, also allows extensive upstream cell culture process development and optimization, e.g. in order to increase viral titer yields (volumetric productivity and/or cell-specific virus yield) and/or to increase product quality, in particular in terms of the proportion of full particles.

In general, upstream cell culture processes can be operated in batch, fed-batch, continuous, or continuous with cell recirculation (perfusion) modes, or hybrid modes (e.g.

hybrid of perfusion and fed-batch). The operational mode determines the growth profile and the production kinetics.

In perfusion mode, feeding of fresh medium (inlet) and removal of spent medium (outlet) are usually done using the same flow rate in the inlet and in the outlet, so that the bioreactor volume is maintained constant. The cells are retained in the production system (bioreactor) by using a cell retention (or perfusion) device. Consequently, high cell densities can be obtained. Typically, perfusion allows for higher volumetric productivity, with lower footprints, compared to other operational modes.

Different perfusion devices can be used, using different mechanisms for cell separation: settling (under gravitational or centrifugal field), aggregation under ultrasonic field (followed by settling), and filtration. Hence, the separation efficiency depends on the selection of the device. Examples are: centrifuges, gravitational settlers (lamella settlers, compact cell settlers), acoustic settlers (aka acoustic filter), centrifuges, hydrocyclones, and filters. Filtration operated under different strategies: TFF (tangential flow filtration) and ATF (alternating tangential flow), floating membranes, spin-filters and rotating cylindrical filters (aka vortex-flow filters or external spin-filters) and rotating disc filters (aka controlled-shear filters). Among the different types of filters, TFF and ATF are commonly used for perfusion. In both cases, a hollow-fiber module containing filter membranes is used. In the case of ATF, the bi-directional flow is obtained through a diaphragm pump. Nowadays, ATF is the mostly used cell retention device for recombinant protein production (biopharmaceuticals). Although perfusion is well established for biopharmaceutical manufacturing processes, it has not yet been available for scalable manufacturing of viral vectors.

In summary, the perfusion process for rAAV production in accordance with the present invention enabled higher titers (vg/L) as well as higher cell-specific virus yield (vg/cell), compared to conventional batch process with stable AAV producer cells. Unexpectedly, when applying perfusion in the stable AAV production system, the ratio between full and empty viral particle was dramatically increased compared to the traditional batch process. In addition, harvesting of the AAV viral vectors could be done from the retentate (whole cell suspension, collected from the bioreactor bulk) instead of the permeate, reducing the volume for the subsequent AAV purification process dramatically, which makes the overall process more efficient.

Utilizing the fully stable AAV producer platform described in the present invention results in a similar percentage of full particles when compared to the fully transient approach. However, this is only true for manufacturing the AAV particle in a batch or fed-batch approach. Unexpectedly, manufacturing AAV viral vectors with the fully stable producer cell system utilizing perfusion advantageously results in a dramatically increased percentage of full particles up to about 10-fold compared to a reference batch process. Therefore, in the subsequent full particle enrichment step by utilizing e.g. AEX chromatography, a final proportion of 75% or higher of full particles can be achieved.

The figures show:

FIG. 1:

Growth of a stable CAP AAV producer in shake flasks (SF) in pseudo-perfusion mode.

A) Cell growth and viability of cultures in shake flasks (SF) 1 and 2 (biological duplicates) to high cell density.

B) Cell specific perfusion rate (CSPR) calculated with the average VCD of the biological duplicates.

FIG. 2:

Simplified scheme of ATF-based perfusion process for rAAV production.

Continuous addition of fresh medium (feed) and removal of spent medium (permeate) is done. ATF (alternating tangential flow) is shown as perfusion device.

FIG. 3:

ATF-based perfusion process for rAAV production with stable CAP AAV producer cells.

Viable cell density (VCD, solid line) and viability (dashed line) of a CAP AAV producer cell line in perfusion bioreactor. Three independent cultivations: runs 1 (◆), 2 (◇) and 3 (●). Perfusion mode is initiated 3 days after inoculation (grey vertical line). Production of rAAV is started 7 days after inoculation (dashed vertical line). Production phase is carried out up to 5 days post-induction.

FIG. 4:

Conventional batch process for rAAV production with stable CAP AAV producer cells.

Viable cell density (VCD, solid line) and viability (dashed line) of a CAP AAV producer cell line in bioreactor in batch mode. Two independent cultivations: runs 1 (■) and 2 (□). Production of rAAV is started 3 days after inoculation (dashed vertical line).

FIG. 5:

Production of rAAV in perfusion mode compared to batch process with stable CAP AAV producer cells.

Three runs in perfusion mode and two runs in batch mode, with a CAP AAV producer cell line, were done. A) AAV8 genome titers determined by qPCR. B) Concentration of capsids determined by ELISA. Data is normalized to the average value of the two batch processes on day 5 post-induction.

FIG. 6:

Higher percentage of full capsids in perfusion mode with stable CAP AAV producer cells.

Comparison to a batch reference process. The percentage was calculated as ratio of genomic titer (FIG. 5A) to capsid titer (FIG. 5B). Data is normalized to the batch runs. A) Time-course of processes in perfusion mode (n=3) and in batch mode (n=2), where n represents the number of biological replicates. B) Full capsids data is represented as average±standard deviation of biological replicates.

FIG. 7:

Increased cell-specific virus yield (CSVY) in perfusion mode with stable CAP AAV producer cells.

Comparison to a batch reference process. The yield was calculated as ratio of genomic titer at time of harvest to viable cell density at time of induction. Data is represented as average±standard deviation of biological replicates (perfusion: n=3, batch: n=2). Data is normalized to batch on day 5 post-induction.

FIG. 8:

Infectivity of CAP derived AAV particles during production in perfusion and batch.

Data is normalized to day 3 post-induction of each production run.

FIG. 9:

Discontinuation of the ATF-based perfusion process during the AAV production phase results in decreased viable cell density and cell viability post-induction.

Viable cell density (VCD, solid line) and viability (dashed line). Perfusion mode is initiated 3 days after inoculation (grey vertical line). Production of rAAV is started 8 days after inoculation (dashed vertical line). Production phase is done in batch mode until 4 days post-induction.

FIG. 10:

Discontinuation of the ATF-based perfusion process during the AAV production phase results in dramatically decreased AAV titer.

AAV8 genome titers determined by qPCR. Titer of high cell density (HCD)-batch measured at time of harvest. Data is normalized to conventional low cell density (LCD)-batch on day 5 post-induction.

FIG. 11:

ATF-based perfusion process for stable rAAV production with stable HEK293 AAV producer pool cells.

Viable cell density (VCD, solid line) and viability (dashed line) of a stable HEK293 AAV producer pool in perfusion bioreactor (◆). Perfusion is initiated 3 days after inoculation (grey vertical line). Production of rAAV is started 6 days after inoculation (dashed vertical line). Production phase lasts until 4 days post-induction.

FIG. 12:

Stable rAAV production with stable HEK293 AAV producer pool cells in batch mode.

Viable cell density (VCD, solid line) and viability (dashed line) of a stable HEK293 AAV producer pool in batch shake flask (a). Production in batch mode is started 3 days after inoculation (dashed vertical line) and is carried out until 5 days post-induction.

FIG. 13:

Production of rAAV in perfusion mode with stable HEK293 AAV producer pool cells.

One run in perfusion mode and one run in batch mode. A) AAV8 genome titers determined by qPCR. B) Concentration of capsids determined by ELISA. Data is normalized to day 3 post-induction of batch control.

FIG. 14:

Increased cell-specific virus yield (CSVY) in perfusion mode with stable HEK293 AAV producer pool cells.

The yield was calculated as ratio of peak genomic titer to viable cell density at time of induction. The result is normalized to batch control.

FIG. 15:

Higher percentage of full capsids in perfusion mode with stable HEK293 AAV producer pool cells.

Figure 13:
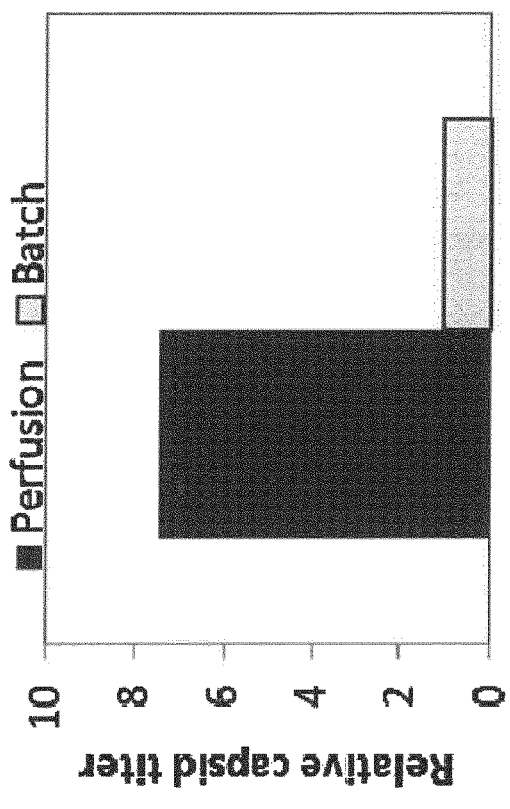
Figure 13:
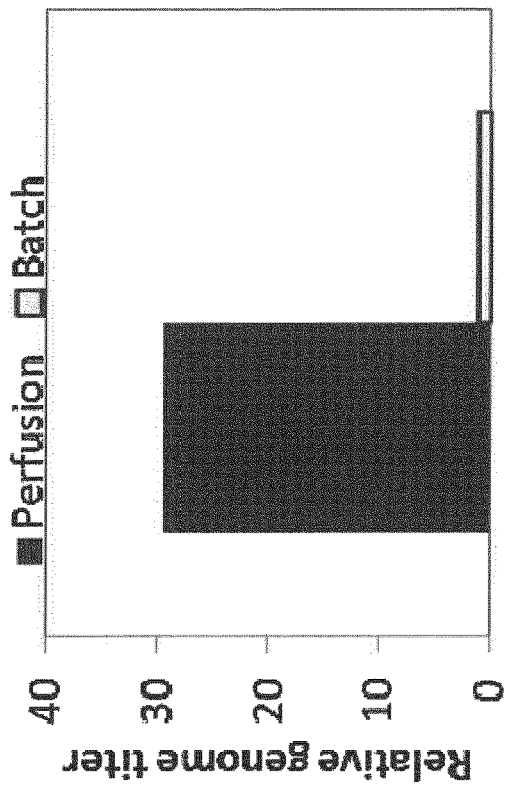

The percentage was calculated as ratio of normalized genomic titer (FIG. 13A) to normalized capsid titer (FIG. 13B). Data is normalized to batch control.

FIG. 16:

SyproRuby staining of AAV particle from different fraction of the AEX runs reveal a ratio of VP1 to VP2 to VP3 of ~1:1:10.

Capsids from different fractions of two different AEX runs were visualized by SyproRuby staining.

FIG. 17:

Full versus empty ratio after AEX purification.

After determination of the viral particle by ELISA and viral genome titer by qPCR, the ratio of full versus empty particle of the different fractions from two AEX runs from an AAV production utilizing ATF perfusion was calculated.

The present invention relates to the following nucleotide sequences:

```
SV40 PolyA Primer forward
                              SEQ ID NO: 1
AGCAATAGCATCACAAATTTCACAA SV40 PolyA Primer reverse
                              SEQ ID NO: 2
CCAGACATGATAAGATACATTGATGAGTT SV40 PolyA Probe
                              SEQ ID NO: 3
AGCATTTTTTCACTGCATTCTAGTTGTGGTTTGTC GFP Primer forward
                              SEQ ID NO: 4
TTCTTCAAGTCCGCCATGCC GFP Primer reverse
                              SEQ ID NO: 5
AAGTCGATGCCCTTCAGCTC GFP Probe
                              SEQ ID NO: 6
CGCACCATCTTCTTCAAGGACGACGGCAACTACA
```

The present invention will be further illustrated by the following examples without being limited thereto.

EXAMPLES

Experimental Procedures

Producer Cell Lines:

Stable AAV producer cell lines harbouring all components necessary for the production of AAV were selected for perfusion process development. Two cell lines were used: (1) based on CAP cells and (2) based on HEK293 cells.

(1) Stable CAP AAV producer single cell clones containing the sequences for the inducer Tet3G, inducible replicase, inducible helper (E2A, E4orf6), VA-RNA, VP1, VP2, and VP3 of the serotype specific capsid (AAV8), and the ITR flanked gene of interest (GOI) GFP. In addition, the Ad5 helper genes E1A and E1B are already stably integrated in the CAP cells as they were immortalized thereby.

(2) Stable HEK293 AAV producer pool containing the sequences for the inducer Tet3G, inducible replicase, inducible helper (E2A, E4orf6), VA-RNA, VP1, VP2, and VP3 of the serotype specific capsid (AAV8), and the ITR flanked gene of interest (GOI) GFP-Luciferase. In addition, the Ad5 helper genes E1A and E1B are already stably integrated in the HEK cells as they were immortalized thereby.

Cell Culture:

(1) For regular cultivation, CAP cells were cultured in Protein Expression Medium (PEM) (Life Technologies/Gibco) supplemented with 4 mM GlutaMAX (Gibco), in non-baffled shake flasks at 37° C., 5% $CO_2$ and 120 to 185 rpm on a shaking incubator. Cells were routinely passaged with fresh medium to a viable cell density of $0.5 \times 10^6$ to $1 \times 10^6$ cells/mL every 3 to 4 days.

(2) For regular cultivation, HEK293 cells were cultured in Protein Expression Medium (PEM) (Life Technologies/Gibco) supplemented with 4 mM GlutaMAX (Gibco), in non-baffled shake flasks at 37° C., 5% $CO_2$ and 170 to 200 rpm on a shaking incubator. Cells were routinely passaged with fresh medium to a viable cell density of $0.3 \times 10^6$ to $0.5 \times 10^6$ cells/mL every 2 to 3 days.

Production of AAV Utilizing Stable AAV Production Platform:

AAV production was induced with addition of doxycycline to the culture.

qPCR to Determine Viral Titer:

The following primer/dual-labelled probe combination (MWG, Eurofins; Table 1) directed against the SV40 PolyA or the GOI (GFP) was used to measure the viral titer.

TABLE 1

| Primer/Probe combinations used for measuring the viral titer | |
| --- | --- |
| Primer/Probe | Sequence |
| SV40 PolyA Primer for | 5'-AGC AAT AGC ATC ACA AAT TTC ACA A-3' (SEQ ID NO: 1) |
| SV40 PolyA Primer rev | 5'-CCA GAC ATG ATA AGA TAC ATT GAT GAG TT-3' (SEQ ID NO: 2) |
| SV40 PolyA Probe | Fam-5'-AGC ATT TTT TTC ACT GCA TTC TAG TTG TGG TTT GTC-3'-BHQ1 (SEQ ID NO: 3) |
| GFP Primer for | 5'-TTC TTC AAG TCC GCC ATG CC-3' (SEQ ID NO: 4) |
| GFP Primer rev | 5'-AAG TCG ATG CCC TTC AGC TC-3' (SEQ ID NO: 5) |
| GFP Probe | Hex-5'-CGC ACC ATC TTC TTC AAG GAC GAC GGC AAC TAC A-3'-BHQ2 (SEQ ID NO: 6) |

Fam: 6-Carboxyfluorescein; BHQ1: Black Hole Quencher; Hex: 5-Hexachloro-fluorescein As standard, linearized transgene plasmid with a defined copy number was used. The qPCR reaction contained the following components: 2×Brilliant Multiplex qPCR Master Mix (Agilent), nuclease-free $H_2O$ (Thermo Fisher Scientific), primer/probe mix and sample/standard. qPCR was run on an Agilent Mx3005P according to the manufacturer's instructions.

ELISA for Assembled Capsids:

ELISA specific for assembled capsids was performed with commercially available ELISA Kits (Progen) according to the manufacturer's instructions.

SDS-PAGE and SyproRuby Staining:

In order to determine the ratio of the capsid proteins VP1, VP2, and VP3, capsid proteins were separated on a SDS PAGE and visualized via SyproRuby staining. Briefly, samples were mixed with 4×LDS buffer and then incubated at 70° C. in a dry heat block for 10 min. The tubes were spun down and the wells loaded with 10 µL sample. 4-12% Bis-Tris gels were run in MES SDS buffer at 200 V for 40 min. SyproRuby staining was performed with overnight incubation in staining solution followed by a 30 min wash step in 10% Methanol, 7% acetic acid and a final wash in ddH₂O.

Separation of Full AAV Particle and Empty AAV Particle Via Anion Exchange Chromatography:

AAV particles from whole cell suspension lysate were enriched chromatography. Full versus empty separation was achieved by utilizing the anion exchange chromatography column.

Example 1

Pseudo-Perfusion Experiment (Cell Growth)

Higher cell densities require higher perfusion rates, using most cell culture media, in order to maintain cell viability and sustain cell growth. As the cell density changes during the production process, the cell specific perfusion rate (CSPR) is a determinant for the perfusion rate during the whole process based on the cell density.

CSPR indicates nutrient supply per cell per day in a continuous process:

$$CSPR = P/VCD,$$

where P=perfusion rate (1/day) and VCD=viable cell density (1×10⁶ cells/mL).

To determine the CSPR for the perfusion bioreactor process, a stable CAP AAV producer (single cell clone) was cultivated in shake flasks in PEM with 4 mM GlutaMAX in non-baffled shake flasks. From cultivation day 3, daily medium exchange was done. After centrifugation, spent medium was discarded. The cell pellet was then resuspended in equal amount of fresh medium. That is, perfusion rate was maintained at 1 vvd until a drop in viability was observed.

Exponential cell growth and high viabilities (>90%) were observed until day 7, corresponding to VCD of 20×10⁶ cells/mL and a CSPR of about 0.05 nL/cell/d (FIG. 1). These parameters were selected as the target for scale-up to perfusion bioreactor. For sustaining higher cell densities using supplemented PEM medium as perfusion medium, higher perfusion rate should be applied.

Example 2

AAV Production in Perfusion Mode Using Stable CAP AAV Producer Single Cells

In order to evaluate the advantages of using an ATF based perfusion over a conventional batch process, the AAV production with stable CAP AAV producer cells was either performed in a batch process or as an ATF-based perfusion process. Both were performed in a stirred-tank bioreactor under controlled conditions.

Conventional Batch Process:

Cells were cultivated in a stirred-tank bioreactor, e.g. the single-use 10c vessel (Eppendorf) vessel, BioFlo320 system (Eppendorf). Bioreactor is inoculated with a comparable low cell density (0.5×10⁶ to 1×10⁶ cells/mL), in PEM medium supplemented with 4 mM GlutaMAX. The process was operated in batch mode. After the cells grew to the target viable cell density for AAV production (typically 3 days post seeding), production of AAV production was initiated with 1 µg/ml doxycycline.

Perfusion Set-Up:

The ATF-based perfusion set-up consisted of a stirred tank bioreactor connected to an ATF unit. Cells were cultivated in a stirred-tank bioreactor, e.g. the single-use 3c vessel (Eppendorf) vessel, BioFlo320 system (Eppendorf).

Perfusion-Based AAV Process:

A bioreactor was inoculated with a comparable low cell density (0.5×10⁶ to 1×10⁶ cells/mL), in PEM medium supplemented with 4 mM GlutaMAX. The process was operated in batch mode for 3 days. Thereafter, perfusion was started, feeding with supplemented PEM medium, following a cell specific perfusion rate (CSPR) of about 0.05 nL/cell/d to about 0.10 nL/cell/d. After the cells grew to about 20×10⁶ viable cells/mL (day 7), induction of AAV production was done with 1 µg/mL doxycycline. During production phase, perfusion rate was maintained approximately constant in about 1 vvd.

Figure 3:
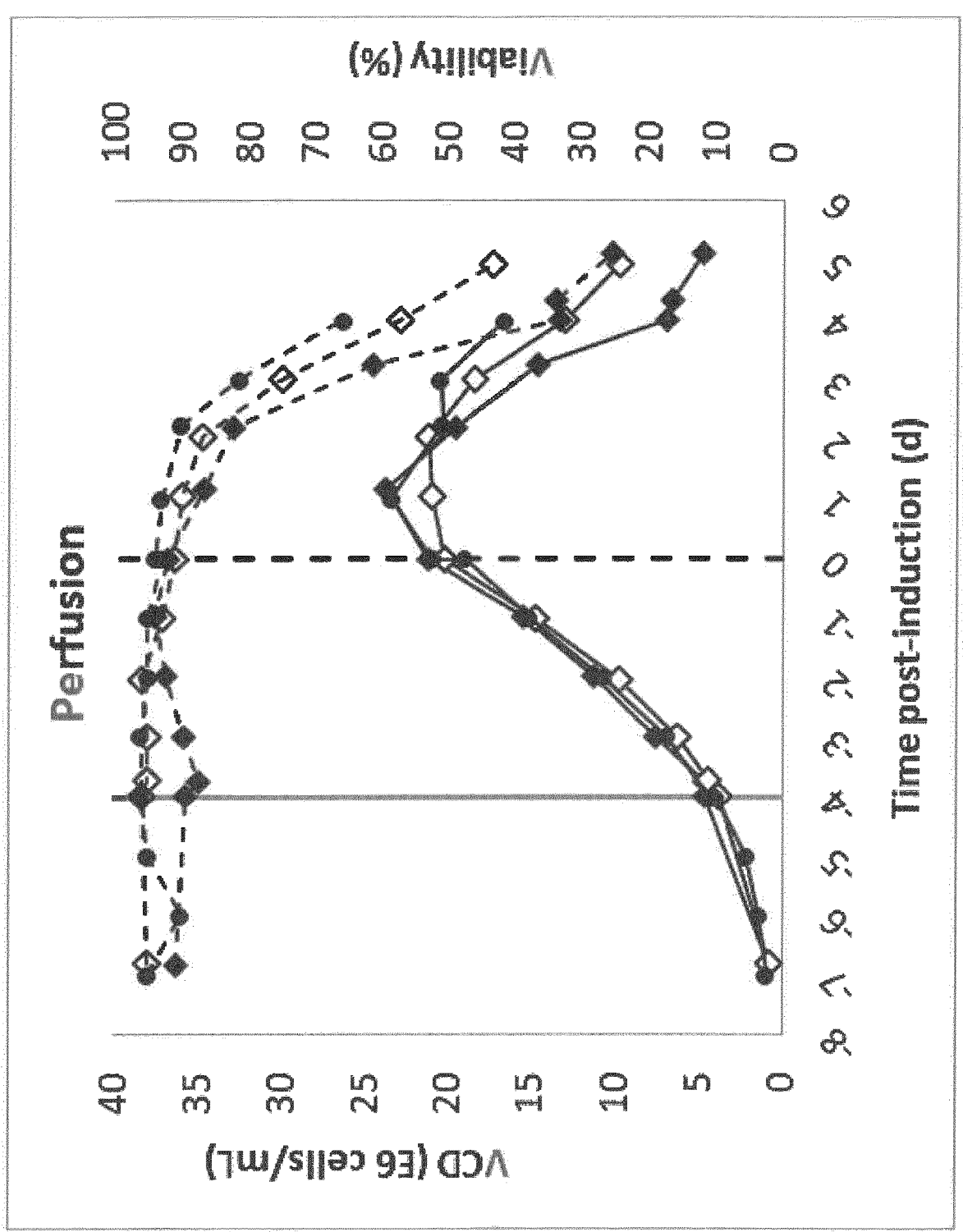
Figure 4:
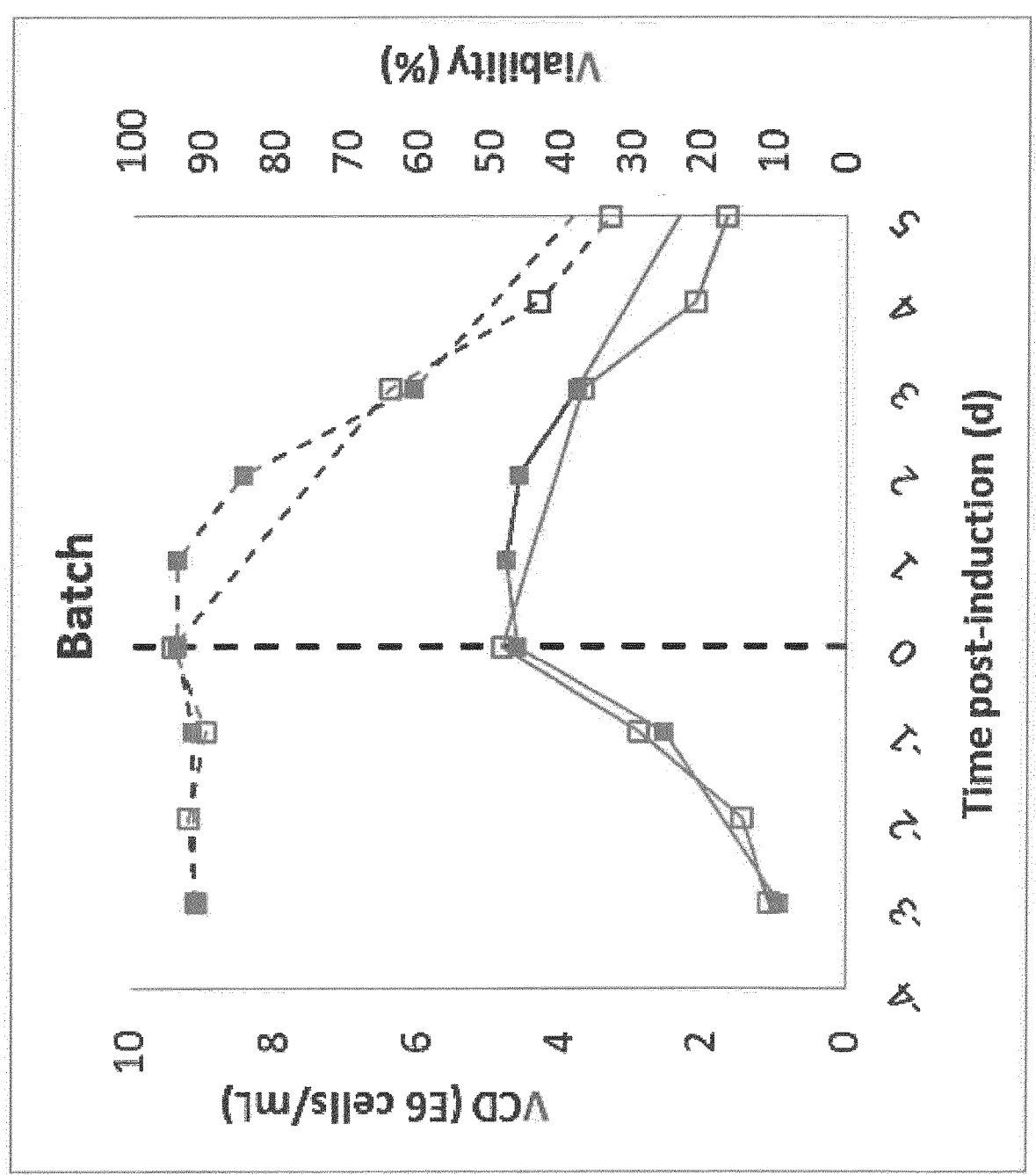

Robust cell growth to 20×10⁶ cells/mL in the three perfusion runs was observed (FIG. 3). Cell growth in perfusion bioreactor was comparable to the semi-perfusion experiment in shake flask (FIG. 1). An approximately 5-fold increase of VCD at time of induction compared to batch process was observed (FIG. 4).

Figure 5:
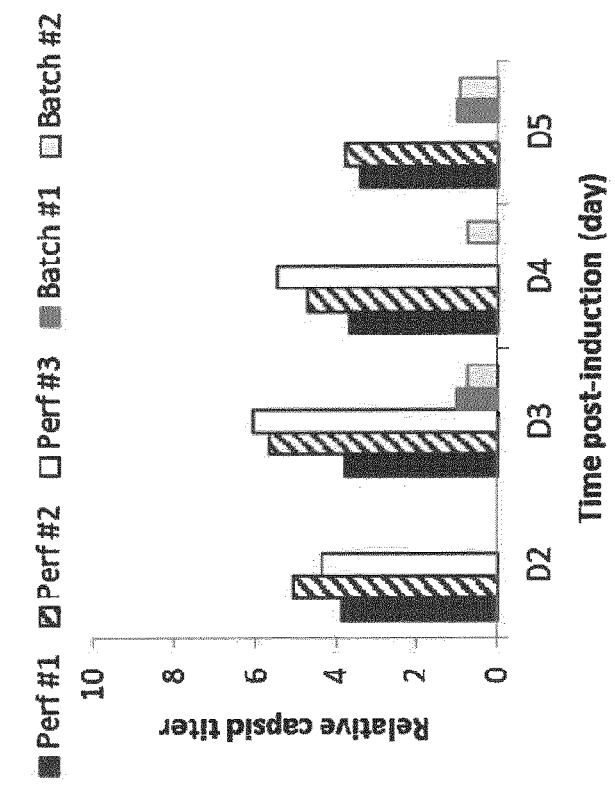
Figure 5:
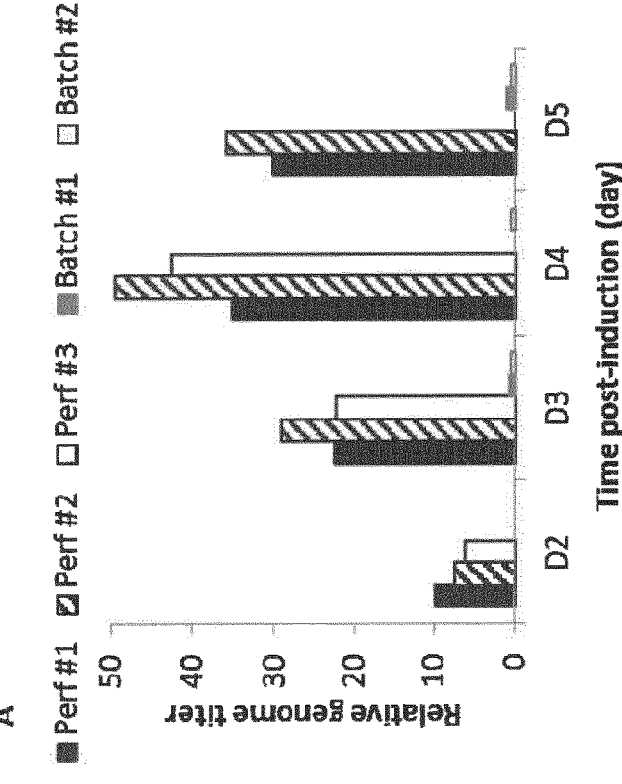
Figure 7:
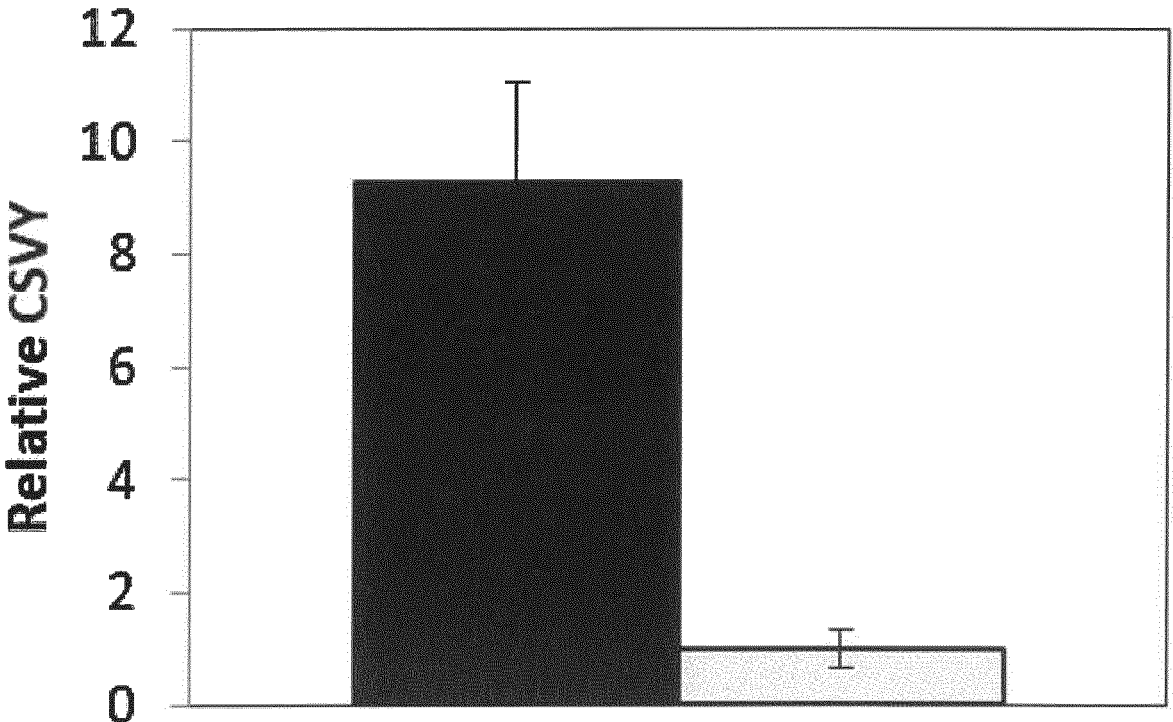

In perfusion mode, genomic titer (vg/mL) was extraordinarily high (FIG. 5). Considering maximum titers, an increase of 42-fold was obtained in the CAP perfusion process (average of three independent cultivations) compared to the reference batch process (average of two independent cultivations). This was partly due to the higher VCD, but more importantly due to a significant increase in the cell-specific virus yield (vg/cell) which was on average 9-fold higher in perfusion (FIG. 7).

Figure 6:
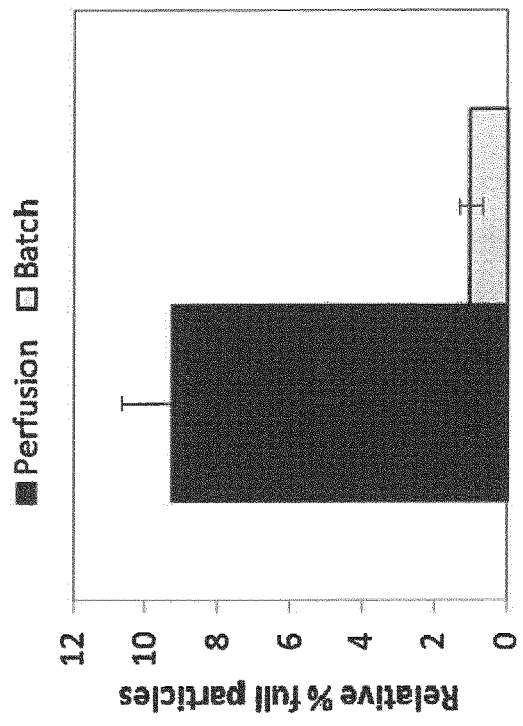
Figure 6:
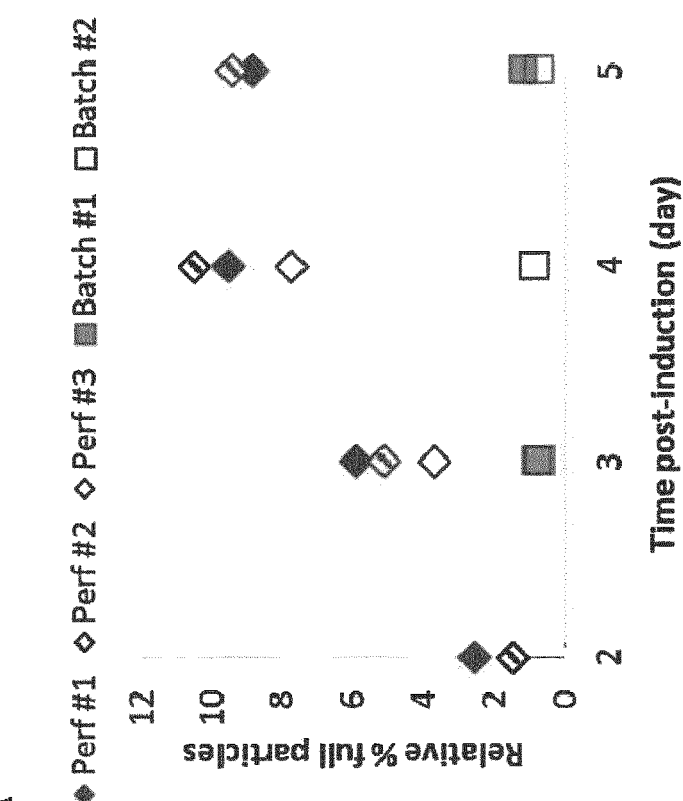

Unexpectedly, the proportion of full particles was also significantly increased in the perfusion process (FIG. 6), as compared to the batch process. The maximum percentage of full particles in perfusion (around 4 d.p.i.) was about 10-fold higher compared to the value obtained in the reference batch process at the same time-point. On average, the maximum percentage of full AAV particle was 9.3-fold higher for the perfusion runs, when data of the three perfusion runs and the two batch runs are compared. Possible explanations could be that the perfusion environment contributed to a better AAV vector DNA amplification or to an increased packaging of viral genomes into the AAV particle.

Infectious AAV particles were determined by transduction assay. The ratio of transduction units (TU) to viral genomes (VG) was calculated (TU:VG). For batch run 2, TU:VG was determined from day 3 to day 6 post-induction (d.p.i.). The maximum value was obtained on 3 d.p.i. For perfusion runs 1 and 2, the maximum value was also obtained on 3 d.p.i. The ratio of TU:VG of each sample was therefore normalized to 3 d.p.i. for each run.

Figure 8:
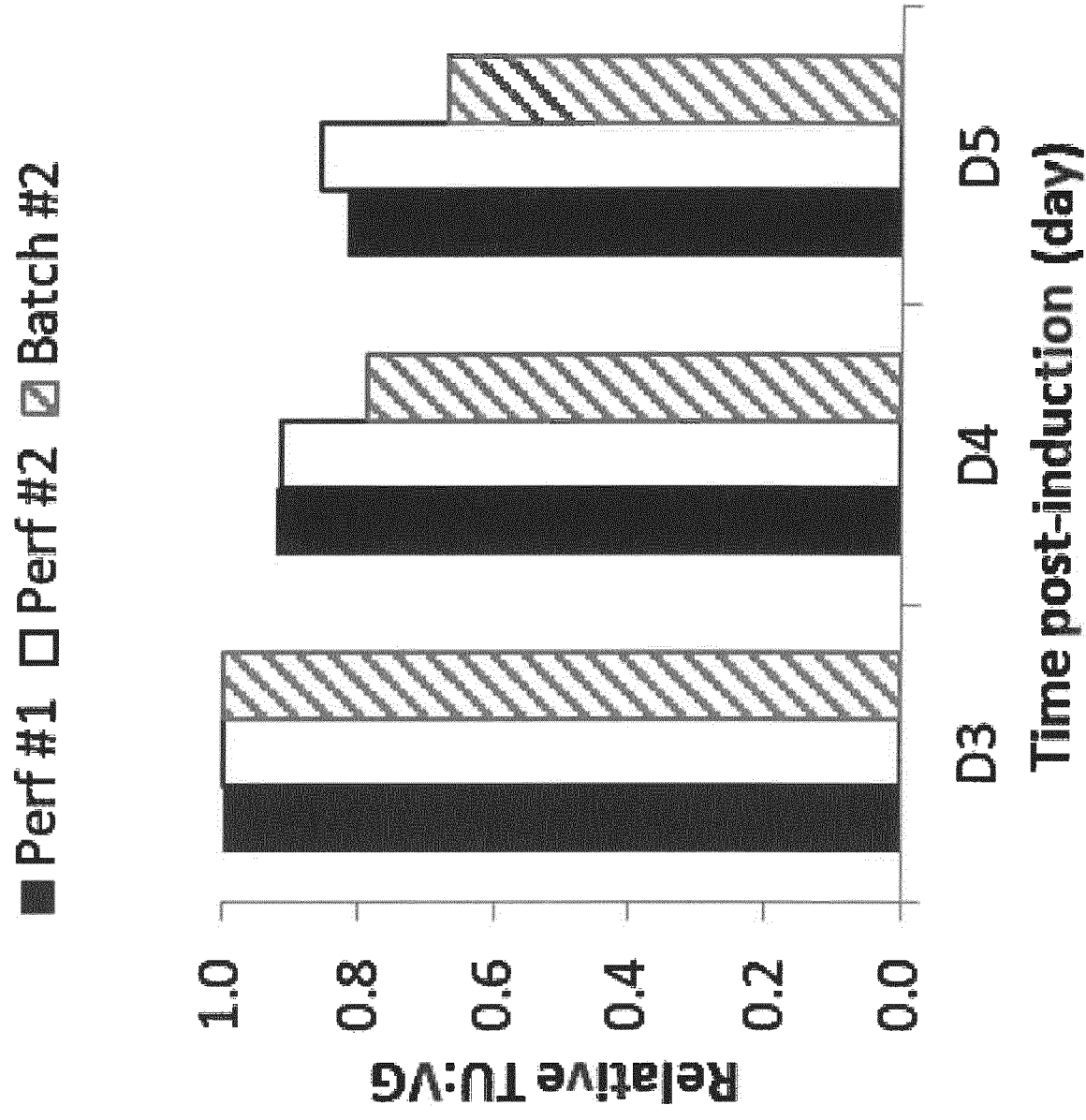

The result (FIG. 8) suggests that higher infectivity was maintained over time in perfusion mode compared to batch. Between days 3 to 5 post-induction, about 30% of infectious AAV particles lost infectivity in batch, while in perfusion mode (1 vvd), the loss was below 18% for the same period.

Example 3

Utilizing ATF Perfusion for Generation of a High Cell Density CAP Producer Cell Culture In order to determine if the significant increase in cell specific productivity, increase of volumetric titer, as well as the increase in percentage of full particle was mainly due to the perfusion mode before induction of AAV production, the following experiment was conducted. The cells were cultured in perfusion mode in the N bioreactor as described in Example 2 until the target viable cell density of $20\times10^6$ cells/mL was reached. However, directly after induction of AAV production by doxycycline induction, the perfusion was stopped and the production phase was operated in batch mode, that means no further media exchange was performed in the production phase.

Perfusion Set-Up:

The ATF-based perfusion set-up consisted of a stirred tank bioreactor connected to an ATF unit. Cells were cultivated in a stirred-tank bioreactor, e.g., the single-use 3c vessel (Eppendorf) vessel, BioFlo320 system (Eppendorf).

Perfusion/Batch AAV Process:

A bioreactor was inoculated with a comparable low cell density ($0.5\times10^6$ to $1\times10^6$ cells/mL), in PEM medium supplemented with 4 mM GlutaMAX. The process was operated in batch mode for 3 days. Thereafter, perfusion was started, feeding with supplemented PEM medium, following a cell specific perfusion rate (CSPR) of about 0.05 nL/cell/d to about 0.10 nL/cell/d. After the cells grew to about $20\times10^6$ viable cells/mL, induction of AAV production was done with 1 µg/mL doxycycline. After induction, perfusion was stopped.

Figure 9:
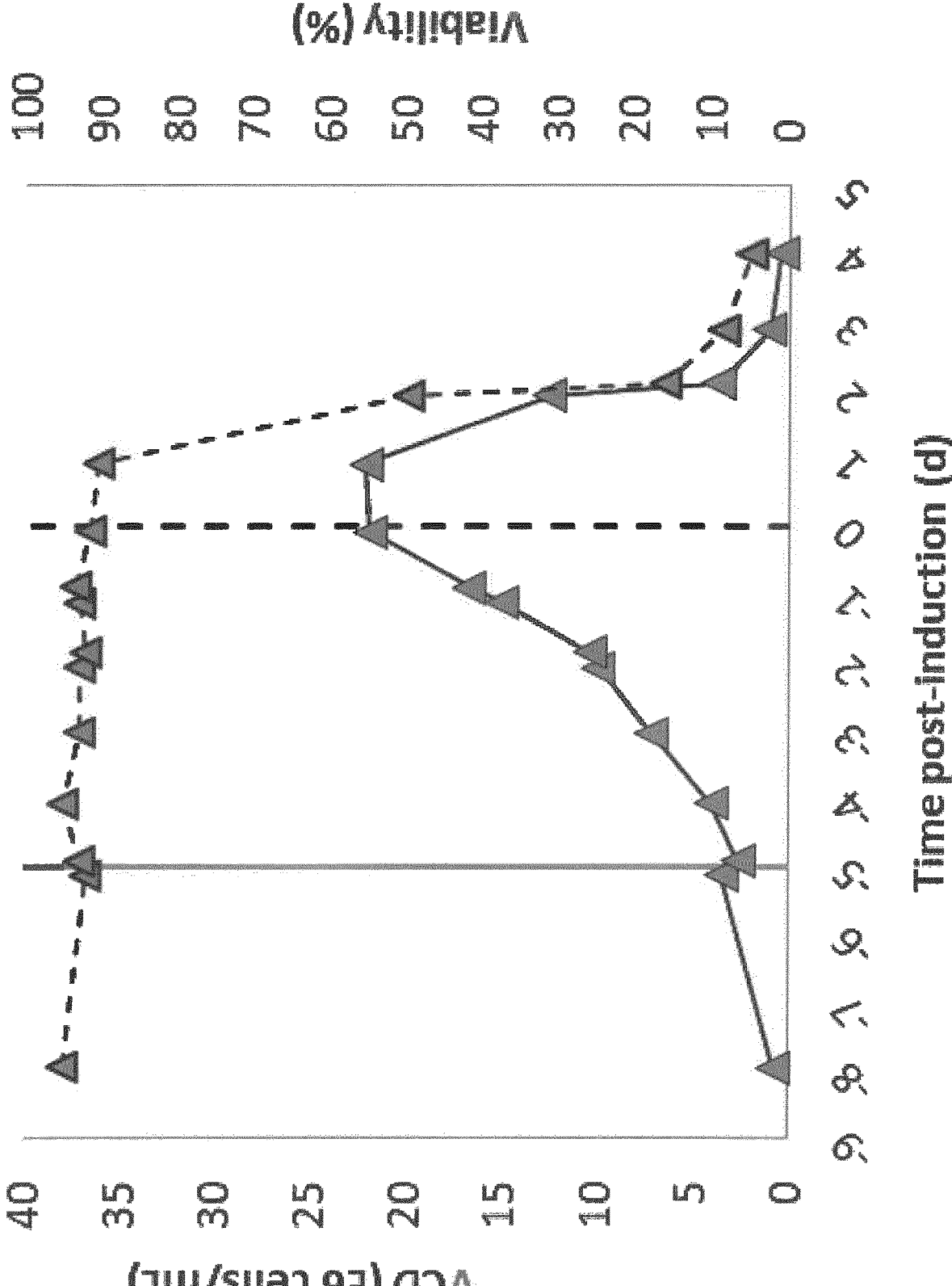
Figure 10:
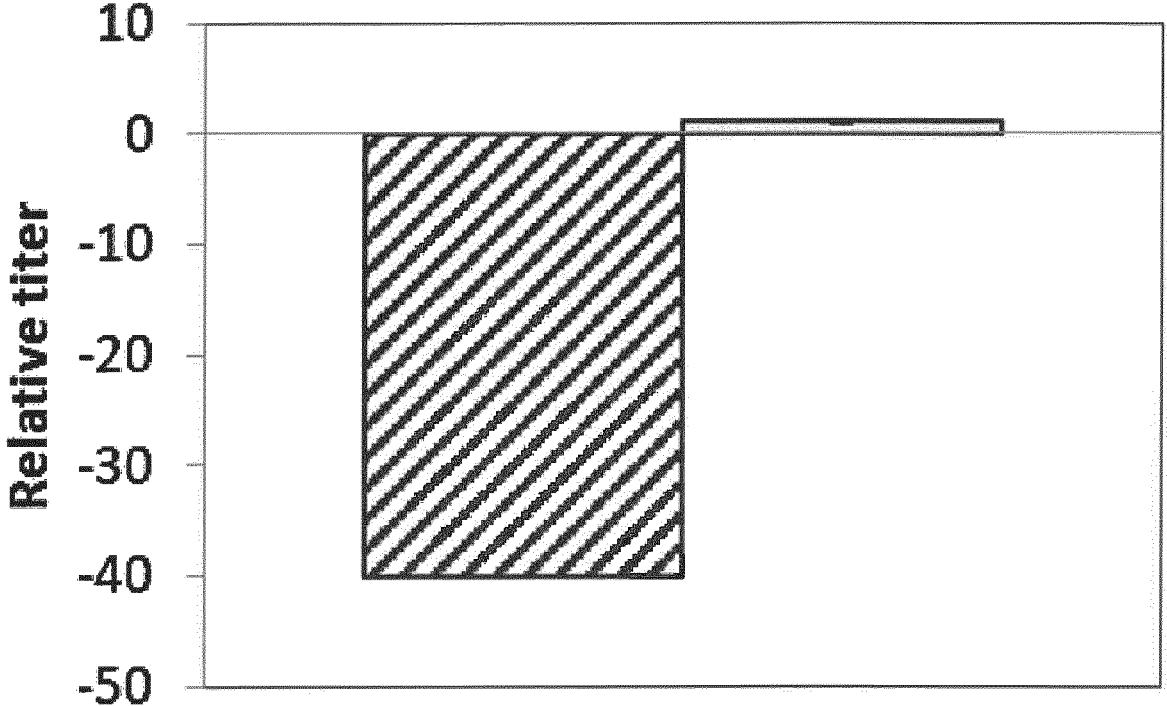

The perfusion culture followed the same growth profile as the previous runs (FIG. 3) and $2.0\times10^6$ cells/mL were reached at the time point of induction (FIG. 9). After the operational mode shift to batch, the cell concentration was maintained for 24 hours post-induction. Subsequently there was a drastic drop in cell concentration and viability. Interestingly, the volumetric as well as cell specific productivity was extremely low, with genome titer 4 days post-induction of about 40-fold lower compared to the reference batch process (FIG. 10). The results indicate that not simply the perfusion mode before the induction and therefore the increase of the viable cell density at the time point of induction is responsible for the astonishing increase in the aforementioned volumetric productivity, cell specific productivity, and increase in percentage of full AAV particle (Example 2).

The results of the present example (Example 3) show clearly that only when the perfusion mode is continued further post-induction and therefore during the whole production phase, ensuring the sustainability of the cells, an efficient AAV production with high cell specific virus yield and increased percentage of full AAV particle is obtained.

Example 4

Perfusion Mode Using Stable HEK293 AAV Producer Cells for AAV Production

This experiment was performed in order to demonstrate that the beneficial effects of the perfusion process in respect to cell specific virus yield, volumetric productivity and the increase percentage of full AAV particle is no limited to stable CAP AAV producer cells (Example 2), but can be transferred to other AAV production systems. Therefore, a similar perfusion process was developed for a stable HEK293 AAV producer pool. As an internal control, AAV was also produced using HEK293 AAV producer pool cells cultured in shake flask and operated in batch mode.

Batch Process:

Cells were cultivated in 125 mL non-baffled shake flask with 30 mL culture volume. The culture was inoculated with a comparable low cell density ($0.5\times10^6$ to $1.0\times10^6$ cells/mL), in PEM medium supplemented with 4 mM GlutaMAX. The process was operated in batch mode. After a 3-day cell growth period, production of AAV production was initiated with 1 µg/mL doxycycline.

Perfusion Set-Up:

The ATF-based perfusion set-up consisted of a stirred tank bioreactor connected to an ATF unit. Cells were cultivated in a stirred-tank bioreactor, e.g. the single-use 3c vessel (Eppendorf) vessel, BioFlo320 system (Eppendorf).

Perfusion-Based AAV Process:

A bioreactor was inoculated with a comparable low cell density ($0.5\times10^6$ to $1\times10^6$ cells/mL), in PEM medium supplemented with 4 mM GlutaMAX. The process was operated in batch mode for 3 days. Thereafter, perfusion was started, feeding with supplemented PEM medium, following a cell specific perfusion rate (CSPR) of about 0.05 nL/cell/d to about 0.10 nL/cell/d. After the cells grew to about $20\times10^6$ viable cells/mL (day 7), induction of AAV production was done with 1 µg/ml doxycycline. During production phase, perfusion rate was maintained approximately constant in about 1.25 vvd.

Figure 11:
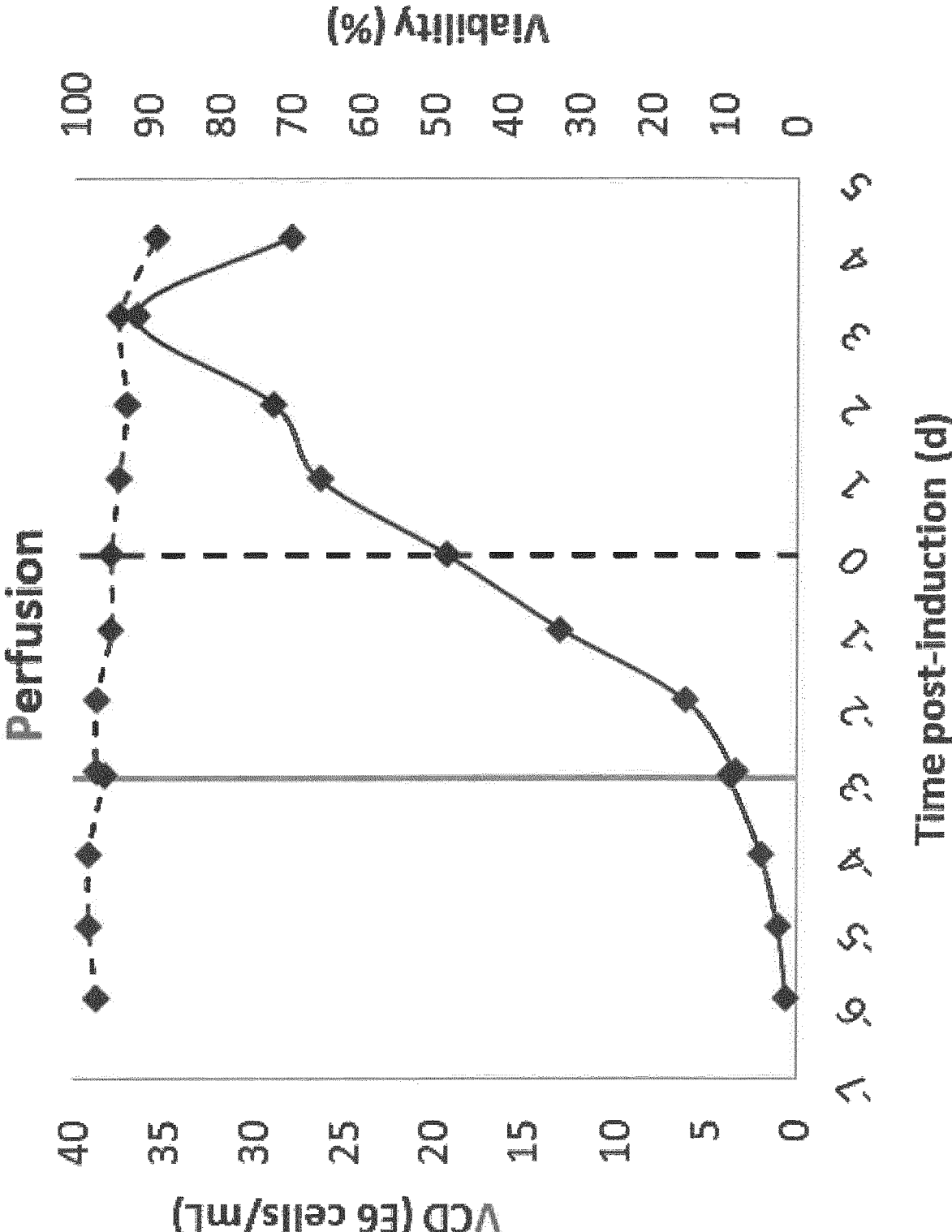
Figure 12:
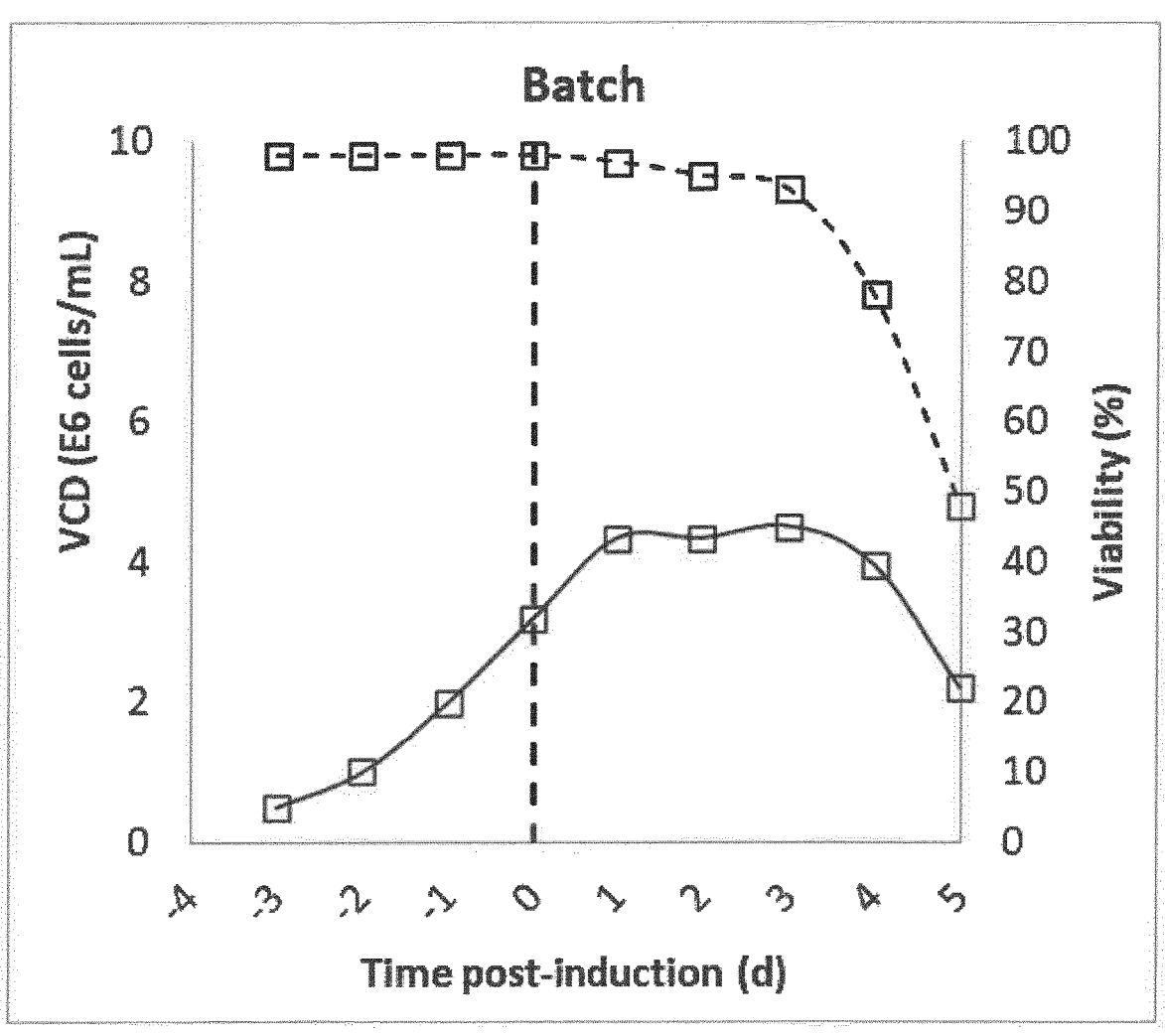

Cell growth to $20\times10^6$ cells/mL in perfusion with high viability was observed before induction (FIG. 11), corresponding to approximately 6 times the viable cell density at time of induction in batch (FIG. 12).

Figure 14:
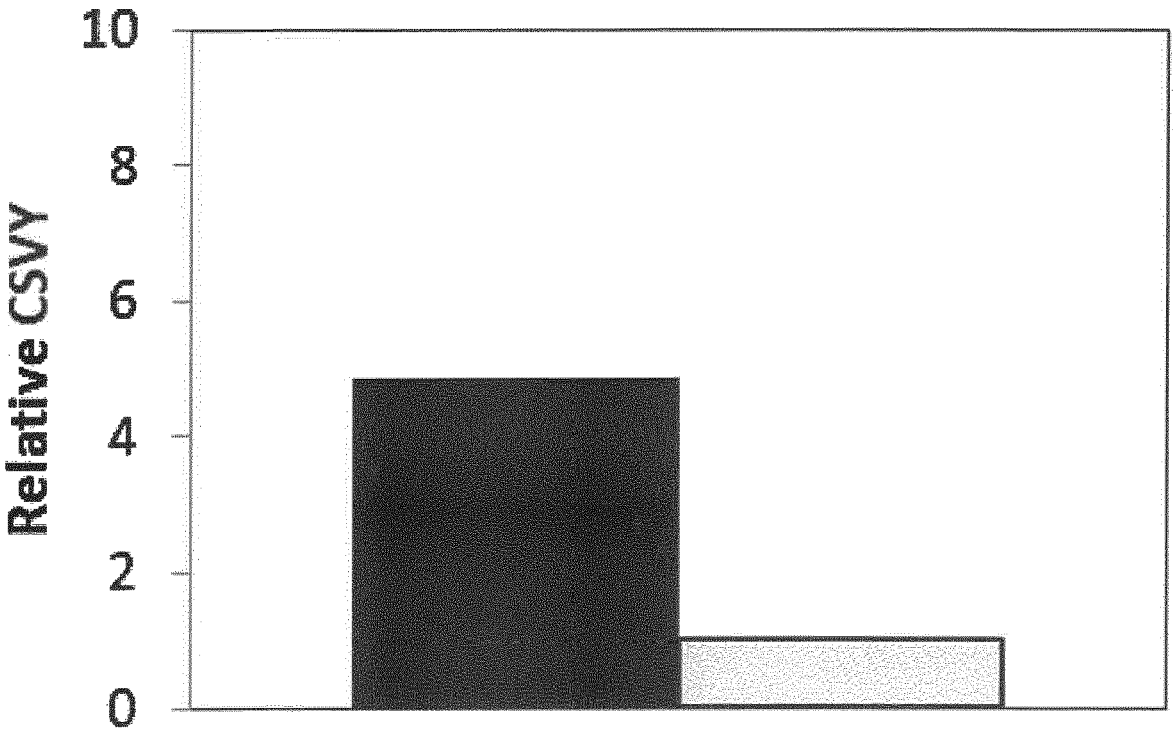

As already seen for the stable CAP AAV producer single cells in Example 2, an enormous increase in volumetric productivity of about 30-fold (FIG. 13) could be achieved by cultivating stable HEK293 AAV producer pool cells in perfusion mode during the entire production phase (i.e., before and after induction of AAV production). Again, the increase in volumetric productivity was not simply due to the increase in the number of viable cells at the time point of induction as this increase was only around 6-fold. Therefore, the overall titer increase was achieved by a 5-fold higher cell-specific virus yield in perfusion mode when compared to batch mode (FIG. 14).

Figure 15:
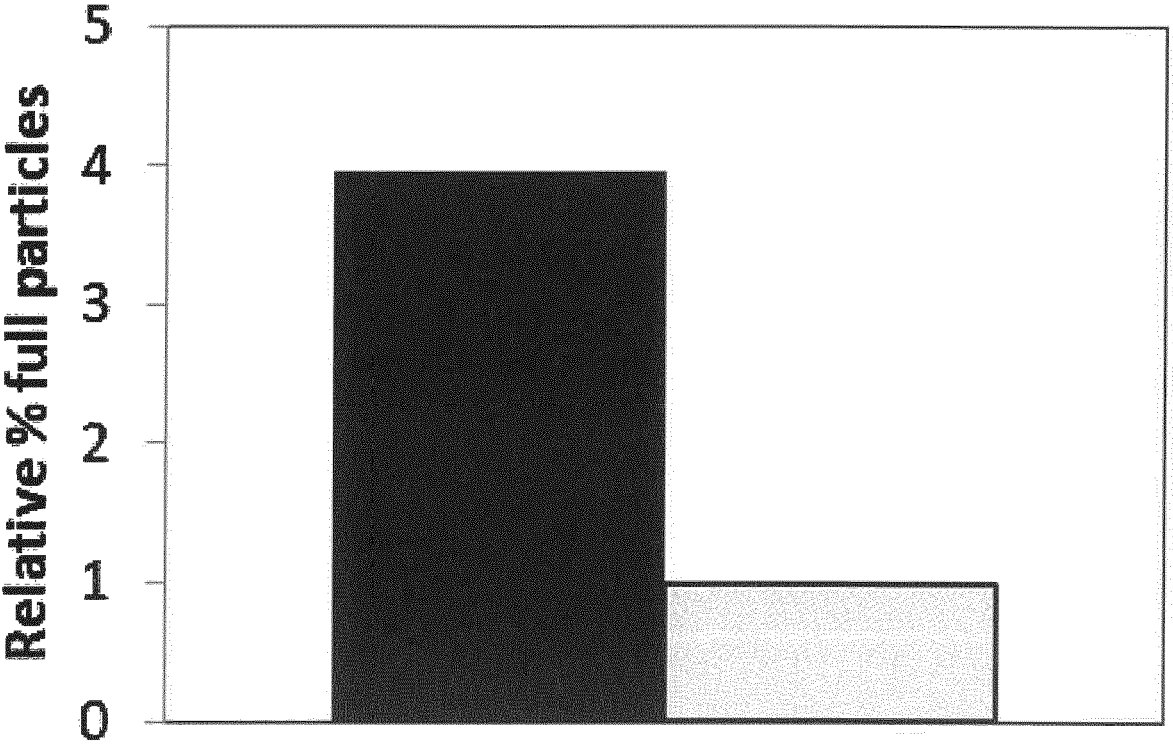

As seen for the stable CAP AAV producer single cells (Example 2), the perfusion process with the stable HEK293 AAV producer pool cells results in an approximately 4-fold increase in the proportion of full AAV particles (FIG. 15) compared to the batch process. The lower fold increase for the stable HEK293 perfusion process compared to the CAP perfusion process is most likely due to the fact that a polyclonal pool was utilized for the HEK293 process, whereas a monoclonal single cell clone was utilized for the CAP perfusion process.

Example 5

Enrichment of Full AAV Particle from Perfusion Material Via AEX

Unexpectedly, it was found that while applying ATF perfusion for the production of AAV particle with a fully stable AAV producer CAP cell line, a significant, about 9-fold increase in the ratio of full particle could be achieved when compared to the conventional batch process.

In order to test if by starting already with higher percentage of full particle, also a further enrichment of full particles utilizing the AEX chromatography can be achieved, the following experiment was performed.

Cell suspension from the retentate of a perfusion run with stable CAP AAV producer cells (Example 2) was lysed and AAV particles were enriched by chromatography. The pooled fractions containing the AAV particles were then subject to anion exchange chromatography. In the elution gradient, full AAV particles were enriched in the fractions 2 for the perfusion AEX run 1 and fractions 5-7 for the perfusion AEX run 2 (FIG. 16).

Figure 16:
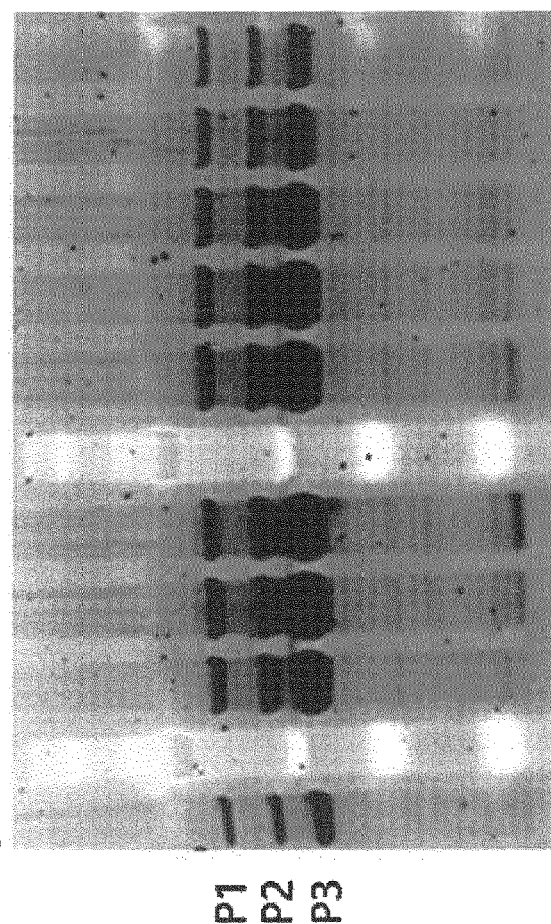
Figure 16:
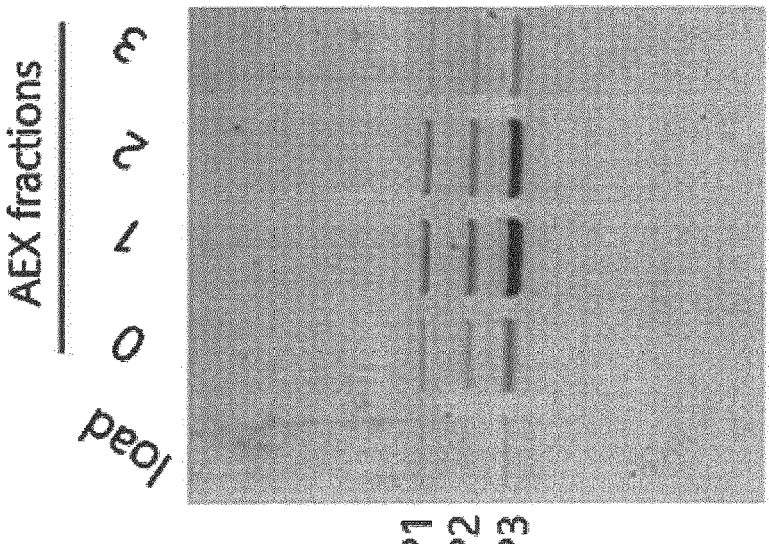

As shown in FIG. 16, the separation of the material from the perfusion process resulted in a percentage of full particles of up to 78%.

Figure 17:
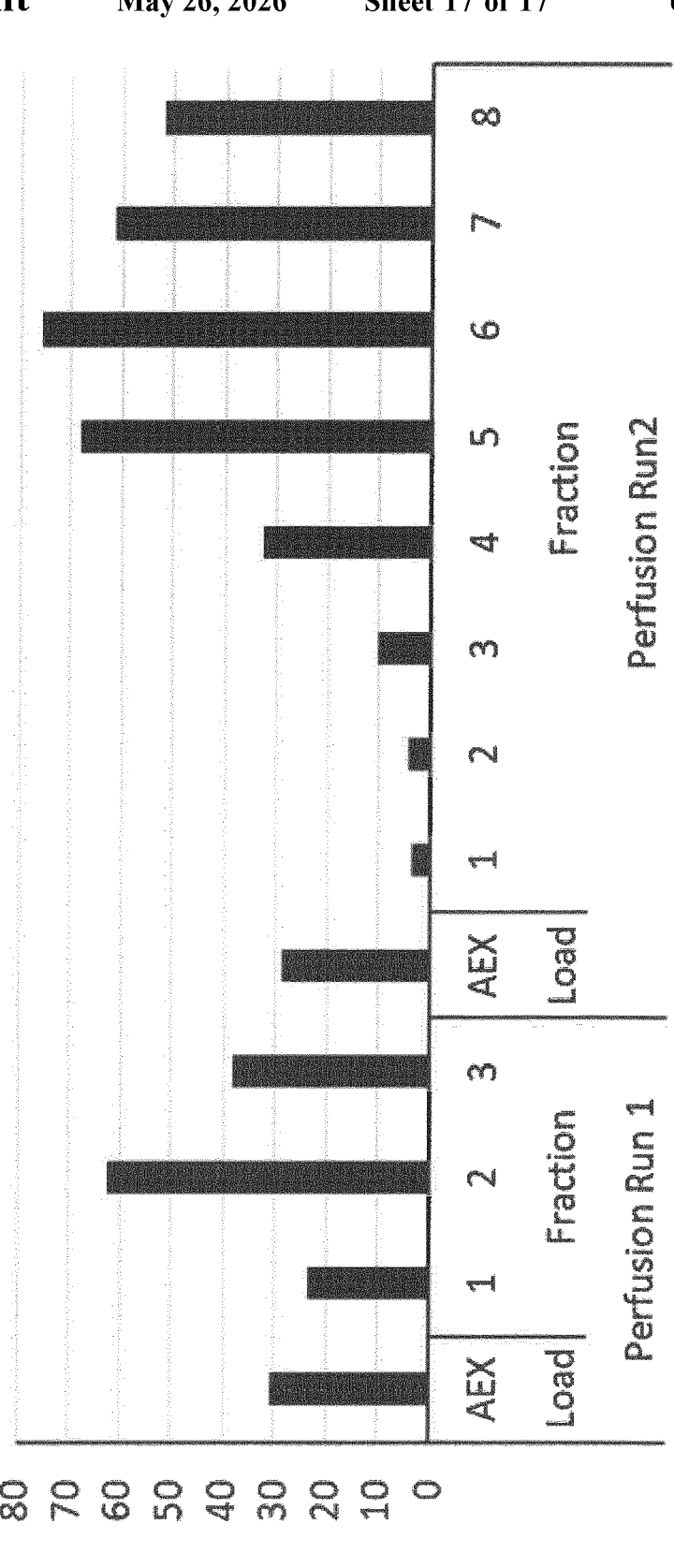

In order to determine the ratio of the capsid proteins VP1, VP2, and VP3, the different fractions from two distinct AEX experiments were separated on a SDS PAGE and visualized via SyproRuby staining. As shown in FIG. 17, over all fractions in both experiments the three capsid proteins displayed the expected ratio of ~1:1:10, proving that the perfusion process is not altering the composition of the AAV capsid.

In summary, this proves that the developed process with ATF perfusion is an outstanding method to ensure high percentage of full AAV particles in the final product.

DISCUSSION

The present invention explicitly shows that the cell specific virus yield is significantly increased in the perfusion process according to the present invention when compared to a batch process (FIG. 7). This proves that the increase in titer seen in the present invention is not only due to an increased viable cell density at the timepoint of induction but is due to an increase in titer per cell.

Further, Example 3 and FIGS. 9 and 10 show a perfusion process in which the viable cell density was increased before induction of AAV production via doxycycline by perfusion process but directly after induction the perfusion process was stopped. Therefore, the production of AAV was in a batch process with high cell densities, proving that the increase in productivity was not just by a high cell density at the timepoint of induction but due to the perfusion process afterwards.

Furthermore, Example 4 and FIGS. 11 to 15 show a perfusion process according to the present invention with stable HEK293 AAV producer cells, proving that the increase in AAV productivity (volumetric and cell specific) and improvement of AAV quality due to a higher full vs. empty ratio is not restricted to CAP cells but also reproducible with another cell line. i.e., HEK293.

Thus, the present invention advantageously provides not only an increase in the cell specific productivity in the methods of the present invention, but also an increase in full vs. empty AAV particles, both of which is unexpected and surprising. These advantageous properties are not due to a mere increase in total cell number, as shown in FIGS. 9 and 10, but results from continued perfusion post-induction.

---

The invention claimed is:

1. A method for the production of Adena-associated virus (AAV), comprising the steps of:
   (a) providing a stable AAV producer host cell line in which at least some or all genes encoding the components necessary for the production of AAV are stably integrated into the host cell genome;
   (b) culturing said cells in perfusion culture during the AAV production step, wherein said perfusion culture encompasses continuous replacement of spent media with fresh media, and wherein said continuous replacement of spent media with fresh media continues after the induction of AAV production,
      wherein at least the following genes are stably integrated into the host cell genome:
         a gene encoding the AAV Rep protein Rep78 or Rep68,
         a gene encoding the AAV Rep protein Rep52 or Rep40; and
         the genes encoding the adenoviral helper functions E4orf6 and E2A.

2. The method according to claim 1, wherein at least the following additional genes are stably integrated into the host cell genome:
   the genes encoding the AAV Cap proteins VP1, VP2, and VP3, and
   the
   the gene of interest (GOI) flanked by AAV ITRs.

3. The method according to claim 1, wherein the AAV is selected from the group consisting of AAV serotype 1 (AAV1), AAV2, AAV3, AAV4, AAV5, AAV6, AAV7, AAV8, AAV9, AAV10, AAV11, AAVDJ, AAVDJ8, AAVrhl0, hybrids of two or more different of said serotypes, and said serotypes having mutations that alter the tropism of the AAV serotype.

4. The method according to claim 1, wherein the genes encoding the components necessary for the production of AAV are selected from the group consisting of genes encoding the AAV Cap proteins VPI, VP2, and VP3; genes encoding the AAV Rep proteins Rep78, Rep68, Rep52, and Rep40; genes encoding the adenoviral helper functions E4orf6, E2A and VA-RNA; genes encoding the Ad5 helper genes EIA and EIB; and the gene of interest (GOI) flanked by AAV inverted terminal repeat sequences (ITRs).

5. The method according to claim 1, wherein the following additional genes are stably integrated into the host cell genome:
   a gene or genes encoding either one or both of the adenoviral helper functions EIA, EIB.

6. The method according to claim 1, wherein the stable AAV producer host cell line is a cell line, selected from the group consisting of CAP cells, AGEI.hn, HEK293, PER.C6, NSOI, COS-7, BHK, CHO, CVI, VERO, HeLa, MDCK, BRL3A, W138, and HepG2 cells.

7. The method according to claim 1, wherein perfusion culture is performed in a stirred-tank bioreactor (STR), orbitally shaken bioreactor (OSB), rocking bed bioreactor, air-lift bioreactor, tubular bioreactor, hollow-fiber bioreactor (HFBR), fixed-bed bioreactor, or fluidized bed bioreactor.

8. The methods according to claim 1, wherein the perfusion device used for perfusion culture is a hollow-fiber filter used in TFF (tangential flow filtration) mode or ATF (alternating tangential flow) mode; a floating membrane, a spin-filter, a rotating cylindrical filter, a rotating disc filter, a centrifuge, a gravitational settler, a lamella settler, a compact cell settler, an acoustic settler, or a hydrocyclone.

9. The method according to claim 8, wherein the perfusion device used for perfusion culture is a hollow-fiber filter used in ATF mode.

10. The method according to claim 1, wherein said continuous replacement of spent media with fresh media continues for at least 24 hours, at least 48 hours, or at least 72 hours after the induction of AAV production, and/or until the harvest of AAV.

11. The method according to claim 1, wherein a cell specific perfusion rate (CSPR) is about 0.01 to about 0.20 nL/cell/day.

12. The method according to claim 1, wherein the perfusion rate is about 1 to about 20 vvd (volume of fresh medium/working volume of reactor/day).

13. The method according to claim 1, wherein the cell density at the seeding of the perfusion culture is about $0.5\times10^6$ to about $5\times10^6$ cells/mL.

14. The method according to claim 1, wherein the cell density at the timepoint of the induction of AAV production is about $20\times10^6$ cells/mL or higher.

15. The method according to claim 1, wherein said method further comprises the step of harvesting AAV from the perfusion culture retentate.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1
agcaatagca tcacaaattt cacaa                                          25

<210> SEQ ID NO 2
<211> LENGTH: 29
<212> TYPE: DNA
<213> ORGANISM: Artificial sequence
<220> FEATURE:
<223> OTHER INFORMATION: Primer

<400> SEQUENCE: 2
ccagacatga taagatacat tgatgagtt                                      29

<210> SEQ ID NO 3
<211> LENGTH: 36
<212> TYPE: DNA
<213> ORGANISM: Artificial sequence
<220> FEATURE:
<223> OTHER INFORMATION: Probe

<400> SEQUENCE: 3
agcatttttt tcactgcatt ctagttgtgg tttgtc                              36

<210> SEQ ID NO 4
<211> LENGTH: 20
<212> TYPE: DNA
<213> ORGANISM: Artificial sequence
```

-continued

```
<220> FEATURE:
<223> OTHER INFORMATION: Primer

<400> SEQUENCE: 4
ttcttcaagt ccgccatgcc                                                     20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
aagtcgatgc ccttcagctc                                                     20

<210> SEQ ID NO 6
<211> LENGTH: 34
<212> TYPE: DNA
<213> ORGANISM: Artificial sequence
<220> FEATURE:
<223> OTHER INFORMATION: Probe

<400> SEQUENCE: 6
cgcaccatct tcttcaagga cgacggcaac taca                                     34
```